(12) United States Patent
Daskivich et al.

(10) Patent No.: US 11,737,683 B2
(45) Date of Patent: Aug. 29, 2023

(54) METHOD AND SYSTEM FOR POSTOPERATIVE AMBULATION MONITORING AND FEEDBACK USING WEARABLE BIOSENSORS

(71) Applicant: CEDARS-SINAI MEDICAL CENTER, Los Angeles, CA (US)

(72) Inventors: Timothy J. Daskivich, Santa Monica, CA (US); Brennan Spiegel, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 135 days.

(21) Appl. No.: 16/761,391

(22) PCT Filed: Nov. 6, 2018

(86) PCT No.: PCT/US2018/059442
§ 371 (c)(1),
(2) Date: May 4, 2020

(87) PCT Pub. No.: WO2019/094381
PCT Pub. Date: May 16, 2019

(65) Prior Publication Data
US 2020/0345273 A1 Nov. 5, 2020

Related U.S. Application Data

(60) Provisional application No. 62/583,388, filed on Nov. 8, 2017.

(51) Int. Cl.
*A61B 5/11* (2006.01)
*A61B 5/00* (2006.01)
(Continued)

(52) U.S. Cl.
CPC ............. *A61B 5/11* (2013.01); *A61B 5/681* (2013.01); *A61B 5/742* (2013.01); *G16H 50/70* (2018.01); *G16H 80/00* (2018.01)

(58) Field of Classification Search
CPC .......... A61B 5/11; A61B 5/681; A61B 5/742; A61B 5/1112; A61B 2505/09;
(Continued)

(56) References Cited

U.S. PATENT DOCUMENTS 10,133,849 B2 * 11/2018 Yanev ................. A61N 1/0452
2010/0262045 A1 10/2010 Heaton et al.
(Continued)

FOREIGN PATENT DOCUMENTS

WO 2017/147652 A1 9/2017
WO 2019/094381 A1 5/2019

OTHER PUBLICATIONS

Appelboom, Geoff et al. "Mobile Phone-Connected Wearable Motion Sensors to Assess Postoperative Mobilization." JMIR mHealth and uHealth vol. 3,3 e78. Jul. 28, 2015, doi:10.2196/mhealth.3785 (Year: 2015).*

(Continued)

*Primary Examiner* — Benjamin S Melhus
(74) *Attorney, Agent, or Firm* — Nixon Peabody LLP

(57) ABSTRACT

A method for monitoring the progress of post-operative ambulation is disclosed. A patient after a surgical procedure such as an operation is provided with an ambulatory routine. The ambulatory routine is monitored using a wearable biosensor device operable to track steps of the patient. The steps of the patient in following the ambulatory routine are recorded. The ambulation data is displayed on a periodic basis to provide feedback to both the patient and health care professionals.

21 Claims, 16 Drawing Sheets

(51) Int. Cl.
*G16H 80/00* (2018.01)
*G16H 50/70* (2018.01)

(58) Field of Classification Search
CPC .......... A61B 2562/0219; A61B 5/0022; A61B
5/024; A61B 5/1118; A61B 5/222; A61B
2560/0214; A61B 2560/0242; A61B
5/0002; A61B 5/02055; A61B 5/021;
A61B 5/1117; A61B 5/112; A61B 5/113;
A61B 5/14532; A61B 5/4809; A61B
5/4812; A61B 5/4815; A61B 5/4848;
A61B 5/6838; A61B 5/72; A61B 5/7264;
A61B 5/7275; A61B 5/743; A61B 5/744;
A61B 5/746; G16H 50/70; G16H 80/00;
G16H 20/30; G16H 40/67; G16H 40/20;
G16H 50/30; G16H 10/60; G16H 40/63;
G16H 50/20
USPC ........................................................ 600/595
See application file for complete search history.

(56) References Cited

U.S. PATENT DOCUMENTS

| | | | |
|---|---|---|---|
| 2012/0290217 A1* | 11/2012 | Shoval .................. | G16H 40/67 702/19 |
| 2014/0039841 A1* | 2/2014 | Yuen ..................... | G01P 13/00 702/189 |
| 2014/0108137 A1* | 4/2014 | Kuri ...................... | G01C 21/00 701/538 |
| 2015/0305654 A1* | 10/2015 | Friedman ............... | A61B 5/742 340/870.07 |
| 2017/0143261 A1* | 5/2017 | Wiedenhoefer ........ | A61B 5/686 |
| 2019/0108909 A1* | 4/2019 | Lee ...................... | G01C 21/3484 |

OTHER PUBLICATIONS

Wayback Machine Archive of Fitbit Review Article—CNet.com (Year: 2016).*
Timothy J. Daskivich, Using Fitbit to Monitor Ambulation in Patients After Surgery, https://clinicaltrials.gov/ct2/show/NCT02741895, Apr. 18, 2016.
O'Connell et al., These Shoes Are Made for Walking: Sensitivity Performance Evaluation of Commercial Activity Monitors under the Expected Conditions and Circumstances Required to Achieve the International Daily Step Goal of 10,000 Steps, Plos One, 2016, vol. 11, pp. 1-14.
Thorup et al., Cardiac Patients' Walking Activity Determined by a Step Counter in Cardiac Telerehabilitation: Data From the Intervention Arm of a Randomized Controlled Trial, Journal of Medical Internet Research, 2016, vol. 18(4), pp. 1-22.
Takahashi et al., In-patient step count predicts re-hospitalization after cardiac surgery, Journal of Cardiology, 2015, vol. 66, pp. 286-291.
International Search Report and Written Opinion for PCT/US2018/59442 dated Jan. 17, 2019, 9 Pages.
International Preliminary Report on Patentability for PCT/US2018/59442 dated May 12, 2020, 8 Pages.

* cited by examiner

- Total number of art pieces: 10
    1. Artist: Bruce Nauman | Double Face (1981) | [81 0082]
    2. David Hockney | Wind (1973) | [76 0390]
    3. Robert Rauschenberg | Medallion (1969) | [75 0171]
    4. LA Fine Art Squad | Isle of California [77 0015]
    5. DJ Hall | Sweet Tooth (1990) | [92 0003]
    6. Philip Guston | Studio Corner (1980) | [81 0011]
    7. Philip Guston | Curtains (1980) | [81 0012]
    8. Francine Matarazzo | Untitled 001P2 (1983) | [83 0013]
    9. Ronald Davis | Rotation (1980) | [83 0322]
    10. Ronald Davis | Framed Block (1970) | [76 0850]

PROBABILITY OF LENGTH OF STAY BY STEP COUNT IN AGGREGATE

| Percentile of LOS | Step Count | Probability | Lower 95% CI | Upper 95% CI |
|---|---|---|---|---|
| 70th percentile | 0 | 0.756010566 | 0.280948145 | 0.960895354 |
| 70th percentile | 100 | 0.704372302 | 0.259603393 | 0.941829356 |
| 70th percentile | 200 | 0.647672922 | 0.23648039 | 0.916040441 |
| 70th percentile | 300 | 0.588328404 | 0.21202873 | 0.88358834 |
| 70th percentile | 400 | 0.529262532 | 0.187041678 | 0.846019503 |
| 70th percentile | 500 | 0.473394482 | 0.16263491 | 0.806231524 |
| 70th percentile | 600 | 0.423124637 | 0.140044746 | 0.767634023 |
| 70th percentile | 700 | 0.379477586 | 0.120071753 | 0.732671358 |
| 70th percentile | 800 | 0.342370252 | 0.102986353 | 0.702446656 |
| 70th percentile | 900 | 0.311358824 | 0.088766912 | 0.6772661 |
| 70th percentile | 1.00E+03 | 0.285833494 | 0.077188769 | 0.656955782 |
| 80th percentile | 0 | 0.725336323 | 0.247339026 | 0.954999237 |
| 80th percentile | 100 | 0.682765158 | 0.239672362 | 0.936284641 |
| 80th percentile | 200 | 0.637451937 | 0.229328655 | 0.912196136 |
| 80th percentile | 300 | 0.590874758 | 0.216173989 | 0.883218607 |
| 80th percentile | 400 | 0.544718178 | 0.200446392 | 0.850967638 |
| 80th percentile | 500 | 0.500672478 | 0.182869597 | 0.81793293 |
| 80th percentile | 600 | 0.460217081 | 0.164600017 | 0.786751571 |
| 80th percentile | 700 | 0.424054525 | 0.146766074 | 0.759125646 |
| 80th percentile | 800 | 0.392233452 | 0.13017508 | 0.735662422 |
| 80th percentile | 900 | 0.364604115 | 0.115340045 | 0.716353794 |
| 80th percentile | 1.00E+03 | 0.34090191 | 0.102485216 | 0.700851488 |
| 90th percentile | 0 | 0.246082098 | 0.025068287 | 0.80557774 |
| 90th percentile | 100 | 0.177596124 | 0.018965479 | 0.706935769 |
| 90th percentile | 200 | 0.125575778 | 0.013773239 | 0.596245692 |
| 90th percentile | 300 | 0.088118017 | 0.009634505 | 0.489765431 |
| 90th percentile | 400 | 0.062114689 | 0.006552639 | 0.399397258 |
| 90th percentile | 500 | 0.044468582 | 0.00439813 | 0.32898012 |
| 90th percentile | 600 | 0.032640457 | 0.002966653 | 0.276740925 |
| 90th percentile | 700 | 0.024671067 | 0.002038539 | 0.238520879 |
| 90th percentile | 800 | 0.019206601 | 0.001437642 | 0.210335703 |
| 90th percentile | 900 | 0.015394252 | 0.001045701 | 0.189314175 |
| 90th percentile | 1.00E+03 | 0.012693403 | 7.87E-04 | 0.173487537 |

FIG. 10

APPNENDIX A - PROBABILITY OF LENGTH OF STAY BY SURGERY TYPE

| % of length | Step Count | Surgery Type | Probability | 95% CI Lower | 95% CI Upper Bound |
|---|---|---|---|---|---|
| 70th percentile | 0 | Lung Lobectomy | 0.703549812 | 0.035513243 | 0.993505019 |
| 70th percentile | 100 | Lung Lobectomy | 0.64600746 | 0.030300365 | 0.990704603 |
| 70th percentile | 200 | Lung Lobectomy | 0.584713884 | 0.025601866 | 0.986919483 |
| 70th percentile | 300 | Lung Lobectomy | 0.52258173 | 0.021477722 | 0.98201033 |
| 70th percentile | 400 | Lung Lobectomy | 0.46269771 | 0.017951824 | 0.975942921 |
| 70th percentile | 500 | Lung Lobectomy | 0.407769552 | 0.015015331 | 0.968846123 |
| 70th percentile | 600 | Lung Lobectomy | 0.359708305 | 0.01263193 | 0.961042763 |
| 70th percentile | 700 | Lung Lobectomy | 0.318985674 | 0.010724894 | 0.952913178 |
| 70th percentile | 800 | Lung Lobectomy | 0.285076032 | 0.009204359 | 0.944798973 |
| 70th percentile | 900 | Lung Lobectomy | 0.25722437 | 0.007994877 | 0.937028809 |
| 70th percentile | 1.00E+03 | Lung Lobectomy | 0.234624959 | 0.007034844 | 0.929894171 |
| 70th percentile | 0 | Gastric Bypass | 0.214220826 | 0.009183629 | 0.88911864 |
| 70th percentile | 100 | Gastric Bypass | 0.17330358 | 0.007628874 | 0.851114797 |
| 70th percentile | 200 | Gastric Bypass | 0.139221265 | 0.006257964 | 0.805976741 |
| 70th percentile | 300 | Gastric Bypass | 0.111695369 | 0.00508696 | 0.755635092 |
| 70th percentile | 400 | Gastric Bypass | 0.090018029 | 0.004117128 | 0.703004036 |
| 70th percentile | 500 | Gastric Bypass | 0.07329645 | 0.003337412 | 0.651348838 |
| 70th percentile | 600 | Gastric Bypass | 0.060622102 | 0.002727898 | 0.603573145 |
| 70th percentile | 700 | Gastric Bypass | 0.051058988 | 0.002258287 | 0.561230579 |
| 70th percentile | 800 | Gastric Bypass | 0.043799376 | 0.001897232 | 0.524670979 |
| 70th percentile | 900 | Gastric Bypass | 0.038258749 | 0.001619888 | 0.493758064 |
| 70th percentile | 1.00E+03 | Gastric Bypass | 0.034016352 | 0.001407065 | 0.468101012 |
| 70th percentile | 0 | Hip Replacement | 0.756010566 | 0.280948145 | 0.960895354 |
| 70th percentile | 100 | Hip Replacement | 0.704372302 | 0.259603393 | 0.941829356 |
| 70th percentile | 200 | Hip Replacement | 0.647672922 | 0.23648039 | 0.916040441 |
| 70th percentile | 300 | Hip Replacement | 0.588328404 | 0.21202873 | 0.88358834 |
| 70th percentile | 400 | Hip Replacement | 0.529262532 | 0.187041678 | 0.846019503 |
| 70th percentile | 500 | Hip Replacement | 0.473394482 | 0.16263491 | 0.806231524 |
| 70th percentile | 600 | Hip Replacement | 0.423124637 | 0.140044746 | 0.767634023 |
| 70th percentile | 700 | Hip Replacement | 0.379477586 | 0.120071753 | 0.732671358 |
| 70th percentile | 800 | Hip Replacement | 0.342370252 | 0.102986353 | 0.702446656 |
| 70th percentile | 900 | Hip Replacement | 0.311358824 | 0.088766912 | 0.6772661 |
| 70th percentile | 1.00E+03 | Hip Replacement | 0.285833494 | 0.077188769 | 0.656955782 |
| 70th percentile | 0 | Robotic Cystectomy | 0.838441051 | 0.338221575 | 0.981377341 |
| 70th percentile | 100 | Robotic Cystectomy | 0.799624627 | 0.289258965 | 0.975080894 |
| 70th percentile | 200 | Robotic Cystectomy | 0.754835353 | 0.240978269 | 0.96759381 |
| 70th percentile | 300 | Robotic Cystectomy | 0.705328635 | 0.19602914 | 0.959179975 |
| 70th percentile | 400 | Robotic Cystectomy | 0.653153036 | 0.156579512 | 0.950252016 |
| 70th percentile | 500 | Robotic Cystectomy | 0.600901093 | 0.123848083 | 0.941305735 |
| 70th percentile | 600 | Robotic Cystectomy | 0.551265293 | 0.09800411 | 0.932840833 |
| 70th percentile | 700 | Robotic Cystectomy | 0.505994104 | 0.078205722 | 0.925182167 |
| 70th percentile | 800 | Robotic Cystectomy | 0.465802085 | 0.063223344 | 0.918471646 |
| 70th percentile | 900 | Robotic Cystectomy | 0.430936675 | 0.051950927 | 0.912778753 |
| 70th percentile | 1.00E+03 | Robotic Cystectomy | 0.401321247 | 0.043485304 | 0.908124515 |
| 70th percentile | 0 | Open Colectomy | 0.622240493 | 0.282722031 | 0.873153873 |
| 70th percentile | 100 | Open Colectomy | 0.558812646 | 0.241237363 | 0.834601535 |
| 70th percentile | 200 | Open Colectomy | 0.494241339 | 0.198412389 | 0.794158288 |
| 70th percentile | 300 | Open Colectomy | 0.431728551 | 0.157577153 | 0.755240942 |
| 70th percentile | 400 | Open Colectomy | 0.374097653 | 0.121786303 | 0.720363837 |
| 70th percentile | 500 | Open Colectomy | 0.323357571 | 0.092763345 | 0.690740466 |
| 70th percentile | 600 | Open Colectomy | 0.280532658 | 0.070673294 | 0.666578535 |
| 70th percentile | 700 | Open Colectomy | 0.245338997 | 0.054451027 | 0.647303762 |

FIG. 11A

| | | | | | |
|---|---|---|---|---|---|
| 70th percentile | 800 | Open Colectomy | 0.216766376 | 0.042681257 | 0.632081013 |
| 70th percentile | 900 | Open Colectomy | 0.193779579 | 0.034166272 | 0.620219743 |
| 70th percentile | 1.00E+03 | Open Colectomy | 0.17543777 | 0.027992322 | 0.611185224 |
| 70th percentile | 0 | Abdominal Hysterectomy | 0.484374731 | 0.07449409 | 0.916412903 |
| 70th percentile | 100 | Abdominal Hysterectomy | 0.419397867 | 0.064609526 | 0.883099095 |
| 70th percentile | 200 | Abdominal Hysterectomy | 0.35786885 | 0.055087606 | 0.841964145 |
| 70th percentile | 300 | Abdominal Hysterectomy | 0.302295109 | 0.046250321 | 0.794709052 |
| 70th percentile | 400 | Abdominal Hysterectomy | 0.254212947 | 0.038372697 | 0.744358198 |
| 70th percentile | 500 | Abdominal Hysterectomy | 0.214169301 | 0.031640154 | 0.694496878 |
| 70th percentile | 600 | Abdominal Hysterectomy | 0.18191729 | 0.026121883 | 0.648326253 |
| 70th percentile | 700 | Abdominal Hysterectomy | 0.156405748 | 0.02172088 | 0.607564208 |
| 70th percentile | 800 | Abdominal Hysterectomy | 0.136319539 | 0.01825541 | 0.572600077 |
| 70th percentile | 900 | Abdominal Hysterectomy | 0.120550628 | 0.015551587 | 0.543258193 |
| 70th percentile | 1.00E+03 | Abdominal Hysterectomy | 0.10820984 | 0.013457099 | 0.519086462 |
| 70th percentile | 0 | Sleeve Gastrectomy | 0.583760813 | 0.09888382 | 0.947157575 |
| 70th percentile | 100 | Sleeve Gastrectomy | 0.518867788 | 0.086615427 | 0.924609699 |
| 70th percentile | 200 | Sleeve Gastrectomy | 0.454160755 | 0.074673415 | 0.895601105 |
| 70th percentile | 300 | Sleeve Gastrectomy | 0.392780407 | 0.063455215 | 0.860636112 |
| 70th percentile | 400 | Sleeve Gastrectomy | 0.337263015 | 0.053318549 | 0.821368692 |
| 70th percentile | 500 | Sleeve Gastrectomy | 0.289210434 | 0.044528887 | 0.780335526 |
| 70th percentile | 600 | Sleeve Gastrectomy | 0.249242082 | 0.037219097 | 0.740330428 |
| 70th percentile | 700 | Sleeve Gastrectomy | 0.21679108 | 0.031307792 | 0.703318194 |
| 70th percentile | 800 | Sleeve Gastrectomy | 0.190703037 | 0.026593065 | 0.670236475 |
| 70th percentile | 900 | Sleeve Gastrectomy | 0.169880631 | 0.022872683 | 0.641464613 |
| 70th percentile | 1.00E+03 | Sleeve Gastrectomy | 0.153370599 | 0.019963179 | 0.617012968 |
| 70th percentile | 0 | Lap Colectomy | 0.506896053 | 0.171807391 | 0.83590146 |
| 70th percentile | 100 | Lap Colectomy | 0.441484785 | 0.145811835 | 0.785423697 |
| 70th percentile | 200 | Lap Colectomy | 0.378829681 | 0.119886039 | 0.731937035 |
| 70th percentile | 300 | Lap Colectomy | 0.321631296 | 0.095680121 | 0.679963132 |
| 70th percentile | 400 | Lap Colectomy | 0.271671132 | 0.074625711 | 0.633065919 |
| 70th percentile | 500 | Lap Colectomy | 0.229724557 | 0.057508563 | 0.593115229 |
| 70th percentile | 600 | Lap Colectomy | 0.195713464 | 0.044369857 | 0.560502768 |
| 70th percentile | 700 | Lap Colectomy | 0.168666077 | 0.034614551 | 0.534453313 |
| 70th percentile | 800 | Lap Colectomy | 0.14728024 | 0.027454979 | 0.513791813 |
| 70th percentile | 900 | Lap Colectomy | 0.130434918 | 0.022219719 | 0.49751683 |
| 70th percentile | 1.00E+03 | Lap Colectomy | 0.117217139 | 0.018388915 | 0.484840859 |
| 80th percentile | 0 | Lung Lobectomy | 0.492905833 | 0.015330801 | 0.983788413 |
| 80th percentile | 100 | Lung Lobectomy | 0.442022458 | 0.013867843 | 0.97808235 |
| 80th percentile | 200 | Lung Lobectomy | 0.392898465 | 0.012415246 | 0.970859349 |
| 80th percentile | 300 | Lung Lobectomy | 0.347083491 | 0.011015021 | 0.962081188 |
| 80th percentile | 400 | Lung Lobectomy | 0.305739309 | 0.009706376 | 0.951891357 |
| 80th percentile | 500 | Lung Lobectomy | 0.269575623 | 0.008521588 | 0.940645645 |
| 80th percentile | 600 | Lung Lobectomy | 0.238860778 | 0.007482612 | 0.928891943 |
| 80th percentile | 700 | Lung Lobectomy | 0.213221101 | 0.006590963 | 0.91714761 |
| 80th percentile | 800 | Lung Lobectomy | 0.19194825 | 0.005834178 | 0.905797578 |
| 80th percentile | 900 | Lung Lobectomy | 0.174379286 | 0.005197381 | 0.89516159 |
| 80th percentile | 1.00E+03 | Lung Lobectomy | 0.159930639 | 0.004665233 | 0.88548735 |
| 80th percentile | 0 | Gastric Bypass | 0.262168434 | 0.012289179 | 0.910292699 |
| 80th percentile | 100 | Gastric Bypass | 0.224556489 | 0.010890545 | 0.883941278 |
| 80th percentile | 200 | Gastric Bypass | 0.191314 | 0.009519714 | 0.853439442 |
| 80th percentile | 300 | Gastric Bypass | 0.162705543 | 0.008225159 | 0.819923758 |
| 80th percentile | 400 | Gastric Bypass | 0.138659986 | 0.007047771 | 0.784999386 |
| 80th percentile | 500 | Gastric Bypass | 0.118875043 | 0.006016181 | 0.750450257 |
| 80th percentile | 600 | Gastric Bypass | 0.102911489 | 0.005144385 | 0.717910671 |
| 80th percentile | 700 | Gastric Bypass | 0.090136662 | 0.004424484 | 0.688310504 |

FIG. 11B

| | | | | | |
|---|---|---|---|---|---|
| 80th percentile | 800 | Gastric Bypass | 0.079896794 | 0.003836226 | 0.661933473 |
| 80th percentile | 900 | Gastric Bypass | 0.071674155 | 0.003359231 | 0.638803137 |
| 80th percentile | 1.00E+03 | Gastric Bypass | 0.065064767 | 0.002974799 | 0.618789024 |
| 80th percentile | 0 | Hip Replacement | 0.725336323 | 0.247339026 | 0.954999237 |
| 80th percentile | 100 | Hip Replacement | 0.682765158 | 0.239672362 | 0.936284641 |
| 80th percentile | 200 | Hip Replacement | 0.637451937 | 0.229328655 | 0.912196136 |
| 80th percentile | 300 | Hip Replacement | 0.590874758 | 0.216173989 | 0.883218607 |
| 80th percentile | 400 | Hip Replacement | 0.544718178 | 0.200446392 | 0.850967638 |
| 80th percentile | 500 | Hip Replacement | 0.500672478 | 0.182869597 | 0.81793293 |
| 80th percentile | 600 | Hip Replacement | 0.460217081 | 0.164600017 | 0.786751571 |
| 80th percentile | 700 | Hip Replacement | 0.424054525 | 0.146766074 | 0.759125646 |
| 80th percentile | 800 | Hip Replacement | 0.392233452 | 0.13017508 | 0.735662422 |
| 80th percentile | 900 | Hip Replacement | 0.364604115 | 0.115340045 | 0.716353794 |
| 80th percentile | 1.00E+03 | Hip Replacement | 0.34090191 | 0.102485216 | 0.700851488 |
| 80th percentile | 0 | Robotic Cystectomy | 0.411775265 | 0.068006732 | 0.870395047 |
| 80th percentile | 100 | Robotic Cystectomy | 0.36326735 | 0.057338407 | 0.842548676 |
| 80th percentile | 200 | Robotic Cystectomy | 0.317909064 | 0.047233439 | 0.81419053 |
| 80th percentile | 300 | Robotic Cystectomy | 0.27685083 | 0.038166459 | 0.78694549 |
| 80th percentile | 400 | Robotic Cystectomy | 0.240787393 | 0.030440152 | 0.762121269 |
| 80th percentile | 500 | Robotic Cystectomy | 0.209982729 | 0.024154715 | 0.740537752 |
| 80th percentile | 600 | Robotic Cystectomy | 0.184344138 | 0.019238401 | 0.722529708 |
| 80th percentile | 700 | Robotic Cystectomy | 0.163300847 | 0.01547581 | 0.707886122 |
| 80th percentile | 800 | Robotic Cystectomy | 0.146083745 | 0.012614265 | 0.696127853 |
| 80th percentile | 900 | Robotic Cystectomy | 0.132026843 | 0.010441131 | 0.686798736 |
| 80th percentile | 1.00E+03 | Robotic Cystectomy | 0.120574925 | 0.008788425 | 0.679505105 |
| 80th percentile | 0 | Open Colectomy | 0.411231008 | 0.137246521 | 0.754098639 |
| 80th percentile | 100 | Open Colectomy | 0.362747669 | 0.119418491 | 0.704960386 |
| 80th percentile | 200 | Open Colectomy | 0.317421923 | 0.100346194 | 0.659730575 |
| 80th percentile | 300 | Open Colectomy | 0.276401109 | 0.081660277 | 0.621338059 |
| 80th percentile | 400 | Open Colectomy | 0.240376782 | 0.064862688 | 0.590780046 |
| 80th percentile | 500 | Open Colectomy | 0.209610145 | 0.050862372 | 0.567553524 |
| 80th percentile | 600 | Open Colectomy | 0.184006451 | 0.039876517 | 0.550428716 |
| 80th percentile | 700 | Open Colectomy | 0.162994004 | 0.031546602 | 0.537926719 |
| 80th percentile | 800 | Open Colectomy | 0.145803615 | 0.025308334 | 0.528764805 |
| 80th percentile | 900 | Open Colectomy | 0.131769509 | 0.020654558 | 0.522021358 |
| 80th percentile | 1.00E+03 | Open Colectomy | 0.120336818 | 0.017179304 | 0.517051487 |
| 80th percentile | 0 | Abdominal Hysterectomy | 0.274817804 | 0.029391103 | 0.825865283 |
| 80th percentile | 100 | Abdominal Hysterectomy | 0.235971505 | 0.026726993 | 0.776468295 |
| 80th percentile | 200 | Abdominal Hysterectomy | 0.201478239 | 0.023882812 | 0.722372763 |
| 80th percentile | 300 | Abdominal Hysterectomy | 0.171672515 | 0.020987419 | 0.667074174 |
| 80th percentile | 400 | Abdominal Hysterectomy | 0.146533687 | 0.018184124 | 0.61414121 |
| 80th percentile | 500 | Abdominal Hysterectomy | 0.125789342 | 0.015605137 | 0.566356621 |
| 80th percentile | 600 | Abdominal Hysterectomy | 0.109012152 | 0.013347533 | 0.525289261 |
| 80th percentile | 700 | Abdominal Hysterectomy | 0.095560694 | 0.01143929 | 0.491023192 |
| 80th percentile | 800 | Abdominal Hysterectomy | 0.084762039 | 0.00985807 | 0.462790249 |
| 80th percentile | 900 | Abdominal Hysterectomy | 0.076080092 | 0.008566864 | 0.439688151 |
| 80th percentile | 1.00E+03 | Abdominal Hysterectomy | 0.069094653 | 0.007523929 | 0.420859494 |
| 80th percentile | 0 | Sleeve Gastrectomy | 0.606937558 | 0.1092825 | 0.951061109 |
| 80th percentile | 100 | Sleeve Gastrectomy | 0.55721775 | 0.10142894 | 0.933466736 |
| 80th percentile | 200 | Sleeve Gastrectomy | 0.506922351 | 0.092677584 | 0.911875557 |
| 80th percentile | 300 | Sleeve Gastrectomy | 0.457838382 | 0.083370344 | 0.886885476 |
| 80th percentile | 400 | Sleeve Gastrectomy | 0.411618472 | 0.073957769 | 0.859708162 |
| 80th percentile | 500 | Sleeve Gastrectomy | 0.369598243 | 0.064928891 | 0.831941279 |
| 80th percentile | 600 | Sleeve Gastrectomy | 0.332677604 | 0.056717786 | 0.805193965 |
| 80th percentile | 700 | Sleeve Gastrectomy | 0.30094927 | 0.04953999 | 0.780503452 |

FIG. 11C

| | | | | | |
|---|---|---|---|---|---|
| 80th percentile | 800 | Sleeve Gastrectomy | 0.273971677 | 0.043417503 | 0.758298902 |
| 80th percentile | 900 | Sleeve Gastrectomy | 0.251229295 | 0.03829524 | 0.738704958 |
| 80th percentile | 1.00E+03 | Sleeve Gastrectomy | 0.232203917 | 0.034075731 | 0.721654538 |
| 80th percentile | 0 | Lap Colectomy | 0.520432494 | 0.180507414 | 0.842435808 |
| 80th percentile | 100 | Lap Colectomy | 0.469337541 | 0.163276599 | 0.80034308 |
| 80th percentile | 200 | Lap Colectomy | 0.419459949 | 0.143434154 | 0.757141949 |
| 80th percentile | 300 | Lap Colectomy | 0.372447834 | 0.122308129 | 0.716525659 |
| 80th percentile | 400 | Lap Colectomy | 0.32960754 | 0.101628196 | 0.681210801 |
| 80th percentile | 500 | Lap Colectomy | 0.291807284 | 0.0829719 | 0.652351316 |
| 80th percentile | 600 | Lap Colectomy | 0.259459187 | 0.067307283 | 0.629773366 |
| 80th percentile | 700 | Lap Colectomy | 0.232283214 | 0.054760296 | 0.612431884 |
| 80th percentile | 800 | Lap Colectomy | 0.209615239 | 0.044948103 | 0.599111573 |
| 80th percentile | 900 | Lap Colectomy | 0.190811067 | 0.037377188 | 0.58882346 |
| 80th percentile | 1.00E+03 | Lap Colectomy | 0.175289986 | 0.031574656 | 0.58081898 |
| 90th percentile | 0 | Lung Lobectomy | 0.002932615 | 8.63E-31 | 1 |
| 90th percentile | 100 | Lung Lobectomy | 0.001942131 | 5.76E-31 | 1 |
| 90th percentile | 200 | Lung Lobectomy | 0.001292399 | 3.86E-31 | 1 |
| 90th percentile | 300 | Lung Lobectomy | 8.70E-04 | 2.62E-31 | 1 |
| 90th percentile | 400 | Lung Lobectomy | 5.96E-04 | 1.80E-31 | 1 |
| 90th percentile | 500 | Lung Lobectomy | 4.19E-04 | 1.27E-31 | 1 |
| 90th percentile | 600 | Lung Lobectomy | 3.04E-04 | 9.20E-32 | 1 |
| 90th percentile | 700 | Lung Lobectomy | 2.28E-04 | 6.90E-32 | 1 |
| 90th percentile | 800 | Lung Lobectomy | 1.76E-04 | 5.34E-32 | 1 |
| 90th percentile | 900 | Lung Lobectomy | 1.41E-04 | 4.25E-32 | 1 |
| 90th percentile | 1.00E+03 | Lung Lobectomy | 1.16E-04 | 3.49E-32 | 1 |
| 90th percentile | 0 | Gastric Bypass | 0.642761746 | 0.033837094 | 0.989297494 |
| 90th percentile | 100 | Gastric Bypass | 0.543457533 | 0.025646662 | 0.981763051 |
| 90th percentile | 200 | Gastric Bypass | 0.441847653 | 0.018955896 | 0.970089211 |
| 90th percentile | 300 | Gastric Bypass | 0.347545886 | 0.013728112 | 0.953238197 |
| 90th percentile | 400 | Gastric Bypass | 0.26743888 | 0.009814781 | 0.930777291 |
| 90th percentile | 500 | Gastric Bypass | 0.20415982 | 0.006997537 | 0.903277553 |
| 90th percentile | 600 | Gastric Bypass | 0.156827079 | 0.005035129 | 0.872384862 |
| 90th percentile | 700 | Gastric Bypass | 0.122372332 | 0.003688028 | 0.840058089 |
| 90th percentile | 800 | Gastric Bypass | 0.097429449 | 0.002761924 | 0.807962554 |
| 90th percentile | 900 | Gastric Bypass | 0.079346629 | 0.002121674 | 0.777457447 |
| 90th percentile | 1.00E+03 | Gastric Bypass | 0.066179794 | 0.001675616 | 0.749524894 |
| 90th percentile | 0 | Hip Replacement | 0.246082098 | 0.025068287 | 0.80557774 |
| 90th percentile | 100 | Hip Replacement | 0.177596124 | 0.018965479 | 0.706935769 |
| 90th percentile | 200 | Hip Replacement | 0.125575778 | 0.013773239 | 0.596245692 |
| 90th percentile | 300 | Hip Replacement | 0.088118017 | 0.009634505 | 0.489765431 |
| 90th percentile | 400 | Hip Replacement | 0.062114689 | 0.006552639 | 0.399397258 |
| 90th percentile | 500 | Hip Replacement | 0.044468582 | 0.00439813 | 0.32898012 |
| 90th percentile | 600 | Hip Replacement | 0.032640457 | 0.002966653 | 0.276740925 |
| 90th percentile | 700 | Hip Replacement | 0.024671067 | 0.002038539 | 0.238520879 |
| 90th percentile | 800 | Hip Replacement | 0.019206601 | 0.001437642 | 0.210335703 |
| 90th percentile | 900 | Hip Replacement | 0.015394252 | 0.001045701 | 0.189314175 |
| 90th percentile | 1.00E+03 | Hip Replacement | 0.012693403 | 7.87E-04 | 0.173487537 |
| 90th percentile | 0 | Robotic Cystectomy | 0.241601066 | 0.017908016 | 0.847689498 |
| 90th percentile | 100 | Robotic Cystectomy | 0.174074241 | 0.011660909 | 0.790134724 |
| 90th percentile | 200 | Robotic Cystectomy | 0.122931301 | 0.007323254 | 0.726995301 |
| 90th percentile | 300 | Robotic Cystectomy | 0.086184609 | 0.004492923 | 0.663398219 |
| 90th percentile | 400 | Robotic Cystectomy | 0.060713836 | 0.002735205 | 0.603701666 |
| 90th percentile | 500 | Robotic Cystectomy | 0.043447261 | 0.001680551 | 0.550669326 |
| 90th percentile | 600 | Robotic Cystectomy | 0.031881731 | 0.001059704 | 0.50551563 |
| 90th percentile | 700 | Robotic Cystectomy | 0.024092976 | 6.93E-04 | 0.467940732 |

FIG. 11D

| | | | | | |
|---|---|---|---|---|---|
| 90th percentile | 800 | Robotic Cystectomy | 0.018754091 | 4.71E-04 | 0.436919787 |
| 90th percentile | 900 | Robotic Cystectomy | 0.015030185 | 3.33E-04 | 0.411458066 |
| 90th percentile | 1.00E+03 | Robotic Cystectomy | 0.012392406 | 2.45E-04 | 0.390697771 |
| 90th percentile | 0 | Open Colectomy | 0.282939665 | 0.054554865 | 0.729600445 |
| 90th percentile | 100 | Open Colectomy | 0.207012604 | 0.039329138 | 0.624715255 |
| 90th percentile | 200 | Open Colectomy | 0.147925614 | 0.026692629 | 0.523578474 |
| 90th percentile | 300 | Open Colectomy | 0.104598631 | 0.017209793 | 0.437979523 |
| 90th percentile | 400 | Open Colectomy | 0.074127276 | 0.010737565 | 0.371288018 |
| 90th percentile | 500 | Open Colectomy | 0.053262328 | 0.006637975 | 0.321410484 |
| 90th percentile | 600 | Open Colectomy | 0.039191103 | 0.004163607 | 0.284662478 |
| 90th percentile | 700 | Open Colectomy | 0.029671387 | 0.002690318 | 0.257404791 |
| 90th percentile | 800 | Open Colectomy | 0.023125646 | 0.001802623 | 0.236832634 |
| 90th percentile | 900 | Open Colectomy | 0.018550112 | 0.001256871 | 0.221105107 |
| 90th percentile | 1.00E+03 | Open Colectomy | 0.015304188 | 9.13E-04 | 0.209013683 |
| 90th percentile | 0 | Abdominal Hysterectomy | 0.515646565 | 0.050236877 | 0.955411947 |
| 90th percentile | 100 | Abdominal Hysterectomy | 0.413262478 | 0.039567771 | 0.923323134 |
| 90th percentile | 200 | Abdominal Hysterectomy | 0.318986949 | 0.030192114 | 0.875735816 |
| 90th percentile | 300 | Abdominal Hysterectomy | 0.239648311 | 0.022365284 | 0.812815435 |
| 90th percentile | 400 | Abdominal Hysterectomy | 0.177639857 | 0.016182532 | 0.739364387 |
| 90th percentile | 500 | Abdominal Hysterectomy | 0.131785895 | 0.011559245 | 0.663319798 |
| 90th percentile | 600 | Abdominal Hysterectomy | 0.099142154 | 0.008267991 | 0.592298603 |
| 90th percentile | 700 | Abdominal Hysterectomy | 0.076215173 | 0.005989987 | 0.530417574 |
| 90th percentile | 800 | Abdominal Hysterectomy | 0.060036811 | 0.004425947 | 0.478530597 |
| 90th percentile | 900 | Abdominal Hysterectomy | 0.048520945 | 0.003352664 | 0.436002364 |
| 90th percentile | 1.00E+03 | Abdominal Hysterectomy | 0.040245736 | 0.002613006 | 0.401622584 |
| 90th percentile | 0 | Sleeve Gastrectomy | 0.854979403 | 0.2380743 | 0.991090338 |
| 90th percentile | 100 | Sleeve Gastrectomy | 0.795938461 | 0.199813495 | 0.983851709 |
| 90th percentile | 200 | Sleeve Gastrectomy | 0.721750962 | 0.162427779 | 0.971985026 |
| 90th percentile | 300 | Sleeve Gastrectomy | 0.635754943 | 0.12775867 | 0.954125931 |
| 90th percentile | 400 | Sleeve Gastrectomy | 0.54467422 | 0.097529323 | 0.929781154 |
| 90th percentile | 500 | Sleeve Gastrectomy | 0.456692576 | 0.072866208 | 0.899902633 |
| 90th percentile | 600 | Sleeve Gastrectomy | 0.378669853 | 0.053998319 | 0.866792982 |
| 90th percentile | 700 | Sleeve Gastrectomy | 0.313603992 | 0.04018369 | 0.832943438 |
| 90th percentile | 800 | Sleeve Gastrectomy | 0.261287412 | 0.030287959 | 0.800220501 |
| 90th percentile | 900 | Sleeve Gastrectomy | 0.220212712 | 0.023281255 | 0.769890984 |
| 90th percentile | 1.00E+03 | Sleeve Gastrectomy | 0.188455347 | 0.018341076 | 0.742679867 |
| 90th percentile | 0 | Lap Colectomy | 0.40675625 | 0.080594003 | 0.842841102 |
| 90th percentile | 100 | Lap Colectomy | 0.312062912 | 0.061236345 | 0.759298554 |
| 90th percentile | 200 | Lap Colectomy | 0.231754766 | 0.04405137 | 0.663847888 |
| 90th percentile | 300 | Lap Colectomy | 0.168736775 | 0.030091323 | 0.570465833 |
| 90th percentile | 400 | Lap Colectomy | 0.12212939 | 0.019769017 | 0.489710456 |
| 90th percentile | 500 | Lap Colectomy | 0.08905262 | 0.012749959 | 0.425283688 |
| 90th percentile | 600 | Lap Colectomy | 0.066187089 | 0.008264602 | 0.376106671 |
| 90th percentile | 700 | Lap Colectomy | 0.050454258 | 0.005475385 | 0.338982699 |
| 90th percentile | 800 | Lap Colectomy | 0.039510341 | 0.003739442 | 0.310734173 |
| 90th percentile | 900 | Lap Colectomy | 0.031798532 | 0.002646041 | 0.289050707 |
| 90th percentile | 1.00E+03 | Lap Colectomy | 0.026296496 | 0.001945075 | 0.27232971 |

FIG. 11E

METHOD AND SYSTEM FOR POSTOPERATIVE AMBULATION MONITORING AND FEEDBACK USING WEARABLE BIOSENSORS

CROSS-REFERENCE TO RELATED APPLICATIONS

This application is a National Phase of International Application No. PCT/US2018/059442, filed Nov. 6, 2018, which designated the U.S. and that International Application was published under PCT Article 21(2) in English, and which claims priority to U.S. Provisional Application Ser. No. 62/583,388, filed Nov. 8, 2017. The contents of that application are hereby incorporated in their entirety.

TECHNICAL FIELD

This disclosure relates to medical monitoring and more specifically to a method to monitor postoperative ambulation.

BACKGROUND

Ambulatory status is a fundamental factor in management of the postoperative surgical inpatient care process. Not only has the level of ambulation been definitively linked to incidence of deep venous thromboembolism following major surgery, it is also a critical determinant of length of stay and cost of inpatient care. Yet despite its central role in recovery and disposition, daily assessment of ambulation is exceedingly imprecise and is an often neglected component of nursing care, being missed 76%-89% of the time. Most often, assessments of daily ambulation rely on patient reports, which may be inaccurate, or nursing accounts, which are difficult to ascertain due to frequent handoffs in care. Given the high stakes for delayed ambulation, it is valuable for surgeons to know when patients deviate from the expected post-operative ambulation course, so that they can either intervene directly (i.e., by ensuring that daily ambulation orders are executed) or plan early for disposition to a rehab/skilled nursing facility if goals are not attainable.

Ambulation status is a critical piece of data in management of post-operative patients. The fact that surgical progress notes universally document orders for ambulatory status (e.g. out of bed to chair TID, ambulate ad lib) underscores its central importance to post-operative management. This focus on ambulation is not surprising given its association with key surgical outcomes including complications, length of stay, and quality of life. Numerous studies across multiple surgical disciplines since 1948 have documented the association of early ambulation with lower rates of deep venous thrombosis. Early ambulation has also been linked with decreased length of stay and reduced cost of care across several specialties. Remarkably, early ambulation also affects seemingly far-reaching outcomes such as perceived quality of life and psychosocial outcomes such as anxiety, depressive mood, and comfort, and satisfaction.

Healthcare lies on a precipice of transformative change. Buoyed by an explosion of information and computing technologies, healthcare delivery is rapidly evolving from an imprecise, population-based approach into a targeted system that responds to the unique biological, psychological, and social profile of individual patients. Technological advances now permit inexpensive and seamless data collection and processing, allowing previously unimaginable delivery of meaningful data from patients to their providers. Put simply: modern technologies are dramatically transforming healthcare for the better.

For example, the advent of patient-reported informatics ("PRIs"), such as data from wearable biosensors, makes quantitative monitoring of daily ambulation in the postoperative setting both feasible and affordable. Advances in digital health technologies, including mobile health (mHealth) smartphone applications like HealthKit from Apple and Bluetooth-enabled wearable biosensors like Fitbit, permit simple, inexpensive, and secure data collection. The NIH is now examining the role of PRIs in clinical trials as part of the national Precision Medicine Initiative. Yet while quantifying ambulation with PRIs may be achievable, it is unclear if this information will lead to meaningful improvement in management (e.g. increasing fidelity of ordered ambulation regimens) or efficiency (e.g. length of stay and 30-day readmissions) or outcomes (of surgical inpatients).

Wireless health technologies are being increasingly utilized by multiple specialties across the field of medicine. In cardiology, physicians now routinely use mobile outpatient telemetry for real-time, "beat-to-beat" arrhythmia and ischemia monitoring. In sleep medicine, low-cost, wireless home sleep physiology systems are beginning to replace the traditional inpatient sleep study as a cost-effective and accurate measure of sleep architecture. There are hundreds of other examples, and these are featured at the annual Wireless Health Conference. However, wireless health technologies are relatively under-represented in surgery, despite ample opportunities for integration in the most fundamental aspects of surgical care, such as monitoring of bowel function and ambulation. The CORE (Center for Outcomes, Research, and Education) group at Cedars-Sinai recently developed a method for quantification of bowel sounds using highly focused acoustic biosensors, in an effort to predict which patients will tolerate or fail postoperative advancement of diet.

Yet no large-scale, multidisciplinary integration of wireless health technologies in monitoring of daily ambulation has been achieved to date. Instead, attempts in the past to improve daily step count in ambulation have revolved around nursing and patient education. There is currently a nursing-based effort at Cedars Sinai Medical Center, for example, to improve daily ambulation among inpatients and nursing documentation of ambulation. However, no interventions have used quantitative step count goals or feedback loops/step count orders such as a designed walking route to improve precision of ordering, monitoring, and incentivizing daily ambulation.

Thus, there is a need for a method that allows accurate recording of post-operative ambulation. There is a further need for a device having an interface that shows the progress of a patient performing post-operative ambulation. There is a further need for ambulation data from patients to be made available to health care professionals to predict recovery of post-operative patients. There is a further need for ambulation data to be made available to health care professionals to monitor the ambulation from post-operative patients.

SUMMARY

One disclosed example is a method of monitoring ambulation therapy after a medical procedure. A patient is provided with an ambulatory routine. The ambulatory routine is monitored using a wearable biosensor device operable to track steps of the patient. The steps of the patient in following the ambulatory routine are recorded. The ambulation data is displayed on a periodic basis.

Another disclosed example is a method of analyzing ambulation data from patients after a medical procedure. A plurality of patients is assigned a wearable biosensor device after the plurality of patients undergo a medical procedure. The plurality of patients is instructed to adhere to a daily ambulation routine. Step data from the biosensor device associated with each patient of the plurality of patients is recorded. The recorded step data is analyzed to determine the optimal steps for ambulation routine associated with the medical procedure The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The foregoing and other advantages of the present disclosure will become apparent upon reading the following detailed description and upon reference to the drawings.

FIG. 10 is a table showing the probability of length of stay of patients by step count in the aggregate; and FIG. 11A-11E is a table showing the probability of length of stay of patients based on surgery type.

Figure 1:
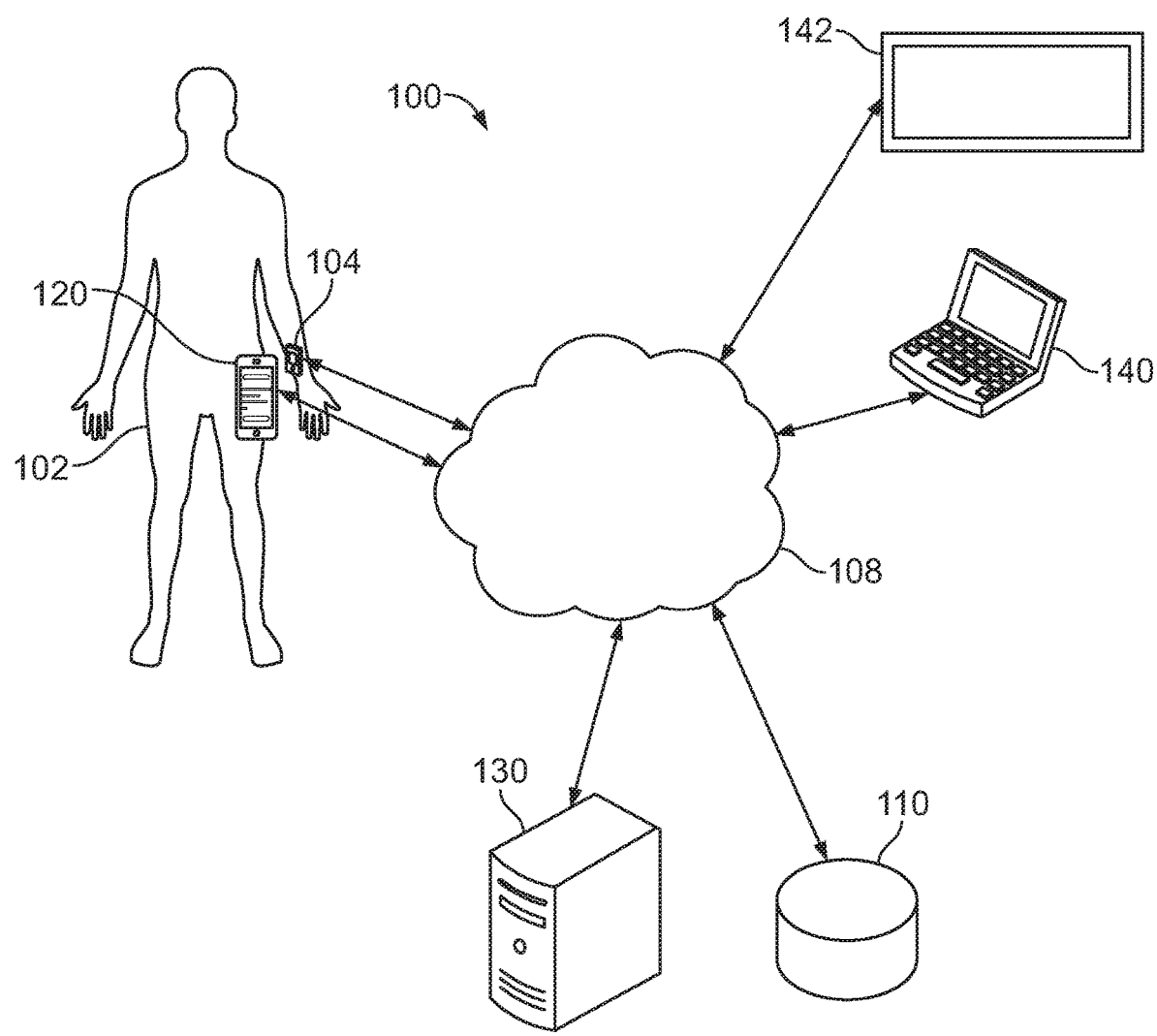
FIG. 1 is a block diagram of a health care environment allowing monitoring of post-operative ambulation by a patient.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

The present examples can be embodied in many different forms. Representative embodiments are shown in the drawings, and will herein be described in detail. The present disclosure is an example or illustration of the principles of the present disclosure, and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed, the singular includes the plural and vice versa; and the word "including" means "including without limitation." Moreover, words of approximation, such as "about," "almost," "substantially," "approximately," and the like, can be used herein to mean "at, near, or nearly at," or "within 3-5% of," or "within acceptable manufacturing tolerances," or any logical combination thereof, for example.

FIG. 1 is a block diagram of a health care system 100 that allows patients and health care professionals to monitor the status of ambulation after a medical procedure. For example, ambulation may be recommended to post-operative patients after major surgeries such as robotic cystectomy, open colectomy, laparoscopic/robotic colectomy, abdominal hysterectomy, lung lobectomy, gastric bypass, hip replacement, and sleeve gastrectomy. A patient 102 may track the progress of ambulation. Further, health care professionals may also monitor the progression of the ambulation and based on the progress predict post-operative recovery. The patient 102 wears a biomonitoring device 104 after a medical procedure such as surgery. The biomonitoring device 104 transmits monitoring data for ambulation to a network 108. The network 108 may be an internal network of the health care institution or the cloud. The data from the biomonitoring device 104 may be uploaded to a cloud storage server 110 periodically and analyzed by applications running on a cloud application server. The patient 102 or health care professionals may access these applications or the output of the applications by accessing the cloud server such as through a website.

An example of a biosensor device 104 is a Fitbit wristband that is an activity monitor that tracks daily activities such as steps taken, distance traveled, calories burned, floors climbed, and active minutes. The Fitbit wristband is the size of a wristwatch, approximately 0.83 inches wide, and comes in three sizes based on wrist size of the wearer. It contains a 3-axis accelerometer, altimeter, and vibration monitor. It is battery powered using a standard lithium-polymer battery, with a battery life of up to 7-10 days with one charge. The device contains sufficient memory to track 7 days of detailed motion data (minute-by-minute) and a daily total for the past 30 days. The wristband is made of a flexible, durable elastomer material and has a stainless steel clasp, similar to that used in many sports watches.

The patient 102 may also carry a portable user device 120 such as a smartphone. Over 80% of the US population now owns a smartphone. Of this majority, 91% keep their phone within 3 feet of their body, 24 hours a day. The ubiquity of smartphones offers a digital portal for patients to collect data about their inputs, health states, and functions. Advances in micro computing and wireless broadband networks enabled development of wearable biosensors such as the biosensor device 104 for everyday use (examples in healthcare from our group and others). Off-the-shelf devices such as Fitbit, Jawbone Up, and the Apple Watch, among others, enable inexpensive and convenient acquisition of free-range activity data, including step counts, stairs climbed, caloric expenditures from exercise, and sleep parameters. Integration of these everyday measurement tools into daily clinical practice represents an opportunity for quantification of data that would have previously been cumbersome or impossible to collect. Furthermore, the opportunity to scale this information is unprecedented due to the ubiquity of the devices among healthcare consumers.

The portable user device 120 in FIG. 1 is in communication with the network 108 and may execute applications that will display the progress of ambulation to the patient 102 in real time. Further, the portable user device 120 may be in wired or wireless communication with the biosensor device 104, such as through radio frequency communication protocols including, for example, WiFi, Zigbee, Bluetooth®, medical telemetry and near-field communication (NFC), and/or optically using, for example, infrared or non-infrared LEDs.

The ambulation data collected by the biosensor device 104 may also be transmitted to a medical server 130 connected to the network 108 that allows health professionals to monitor the status of the ambulation for the patient 102. The patient 102 may also access ambulation data on the portable user device. Further, through connection to the network, ambulation data may be available on other devices such as a computer 140 or television 142 accessible by the patient 102.

Figure 2:
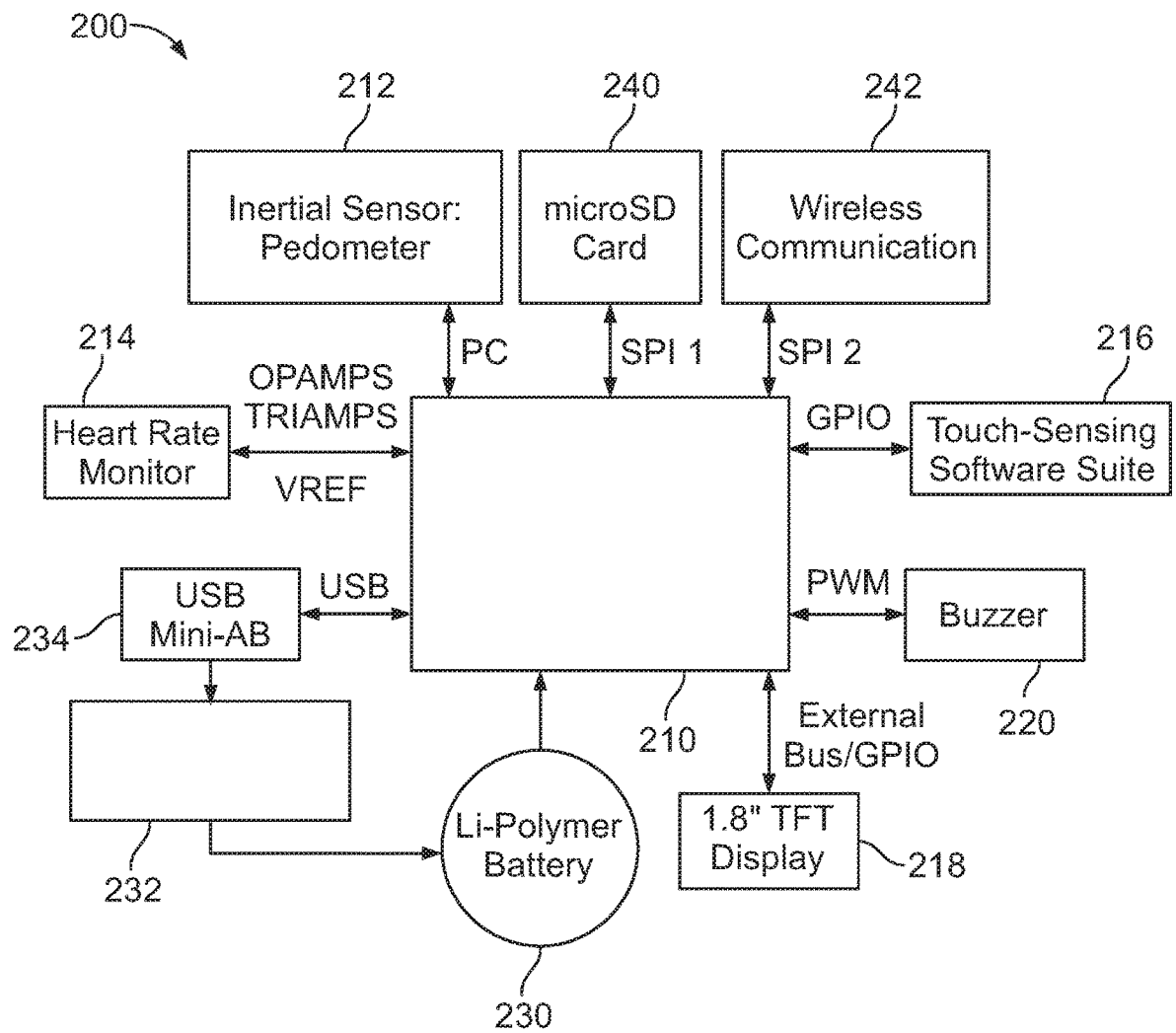
FIG. 2 is a block diagram of the biosensor device in FIG. 1 for monitoring ambulation.

FIG. 2 is a block diagram of a monitoring device 200, such as the biomonitoring device 104, that may be used to generate ambulation data from the patient 102 in FIG. 1. The monitoring device 200 includes a processor 210 that generally supervises the functions of the monitoring device 200 and runs applications to operate the monitoring device. The device 200 includes an inertial sensor 212 that determines steps that correlate with ambulation. The device 200 also includes a heart rate monitor 214 that monitors heart rate. Signals from the inertial sensor 212 and heart rate monitor 214 are sent to the processor 210 for analysis.

A touch sensing suite 216 accepts user inputs and controls to operate the monitoring device 200 and control a display 218. A buzzer 220 may be controlled by the processor 210 to alert a user such as the patient 102. The monitoring device 200 is powered by a lithium battery 230. The battery 230 is coupled to a power management and charging circuit 232 that is coupled to a charging port 234 that may be a USB connection in this example.

Data obtained from the sensors such as the inertial sensor 212 and the heart rate monitor 214 may be stored in a storage device 240. A wireless communication unit 242 allows communication of the data to external devices such as the user device 120 in FIG. 1.

The use of the biosensor device 104 in FIG. 1 addresses the imprecision with which daily step count for ambulation is currently ordered and monitored. As will be explained below, applications for the biosensor device 104 and other devices in FIG. 1 allows for establishment and execution of actionable daily step count goals for the patient 102 to improve clinical outcomes. The disclosed approach below also: (1) permits direct engagement of patients to achieve daily step goals via motivation from a feedback loop; (2) incentivizes patients to ambulate using flexible instructions such as "art tours" that may be displayed on the user device 120; (3) allows medical professionals such as physicians and nursing staff to better assess patient progress towards daily step goals for ambulation; and (4) provides for step count orders that endorse step count as a prescriptive analytic tool for medical professional. Ultimately the below described applications improve adherence to ambulation orders, improve daily step count, and reduce length of stay, deep venous thrombosis rate, and other poor clinical outcomes associated with reduced step count.

This concept is intended for application to monitoring of postoperative ambulation after major surgery, but it is equally applicable to monitoring of ambulation for any hospital inpatient procedure. The predictive models using wearable biosensor devices such as the biosensor device 104 allows for a measured daily step count with specific probabilities of long length of stay that may be utilized by health care institutions such as hospitals for targeting of nursing interventions to prevent poor efficiency outcomes for patients. Further, such quantitative analysis of specific probabilities may assist health care institutions in allocating resources such as rooms to patients over a period of time.

The system also allows real-time feedback loops to engage the patient (including software-based approaches to store and push collected data to in-room TV screens such as the television 142 in FIG. 1. The data processing software running on a cloud based device or server such as the server 130 may generate meaningful visualizations on displays available to the patient and health care professionals. Such data and appropriate software interfaces could be distributed to other hospitals providing inpatient surgical care that may be accessible to patients.

The health care system server 130 includes a patient database that continually gathers ambulation data from patients using wearable biosensors such as the biosensor device 104 in FIG. 1 to monitor post-operative ambulation. The system also improves estimation of metrics surrounding ambulation (e.g. average surgery-specific step count, average surgery-specific length of stay, etc.) that could provide reference data for improving accuracy of using this data as a diagnostic and therapeutic tool. The database could be a subscription service that assists health care professionals or health care institutions such as hospitals understand their performance in post operative patient treatment compared with competitors and intervene in areas needing improvement.

Figure 3A:
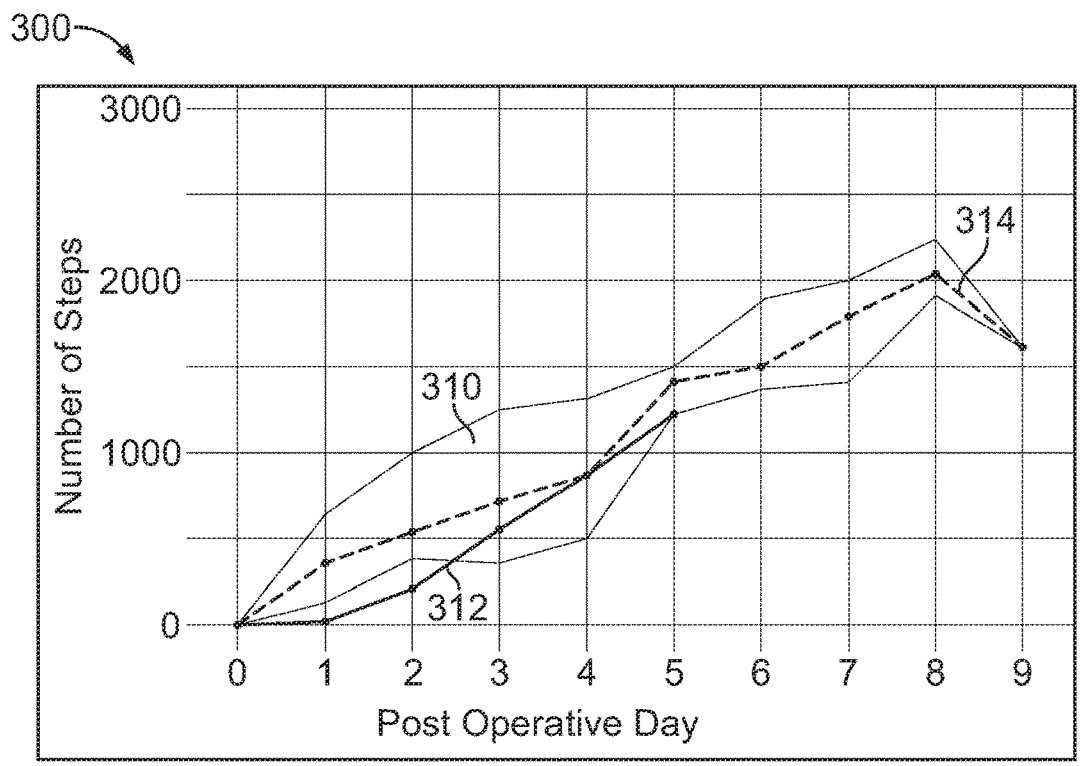
FIG. 3A is a screen image of an interface for ambulation data generated for a patient as compared to an average patient.
Figure 3B:
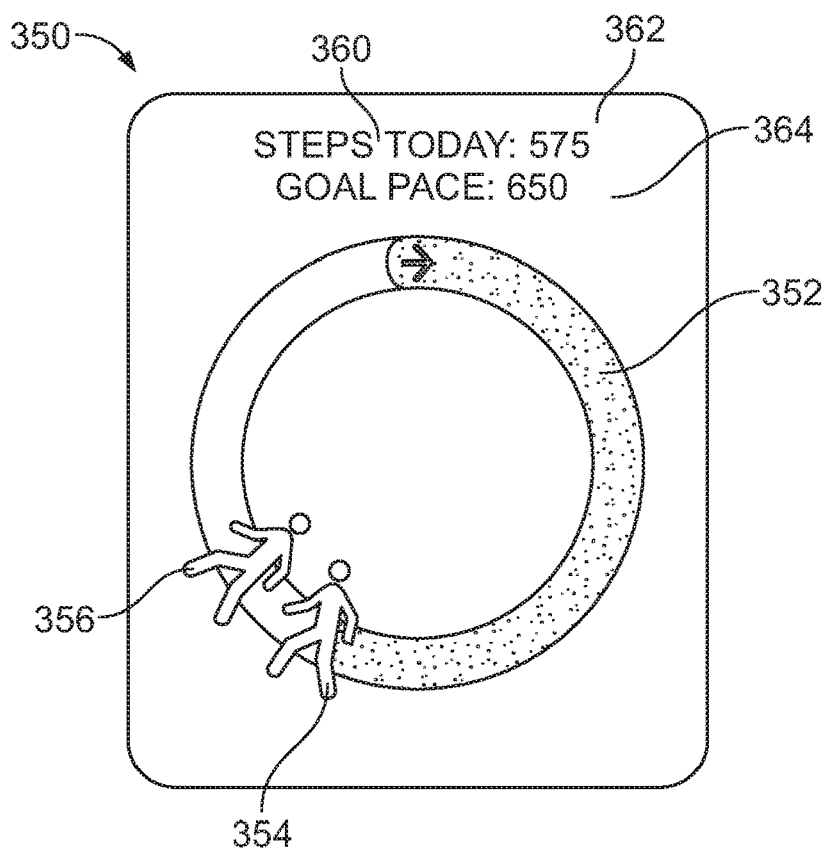
FIG. 3B is a screen image of an interface for ambulation data showing progress toward an ambulation goal for a patient.

FIG. 3A is a screen image of a first interface 300 that may be generated from the data recorded from the patients for ambulation. FIG. 3B is a screen image of another interface 350 that may be generated from the ambulation data recorded from the patients. The application to generate the interfaces 300 and 350 may be run remotely on a server or on a local device such as the user device 120 or computer 140 in FIG. 1. The interfaces 300 and 350 may be displayed and cycled using a remote or other control device of a device such as the television 142 in FIG. 1 or by a user input on devices such as the portable user device 120 or computer 140 in FIG. 1.

The interface 300 in FIG. 3A includes a plot 310 that shows the number of steps against the post operative day. The plot 310 includes a line plot 312 of a daily step count (6 am-6 pm) as measured by the biosensor device 104 in FIG. 1 such as a Fitbit device. The line plot 312 is a solid line that represents the trajectory of the ambulation of the patient after the surgery. A dashed line 314 represents the standard trajectory of an average patient after the specific surgery performed on the patient. The standard trajectory represented by the dashed line 314 is static for any given surgery but varies across surgery type. The line plot 312 for the patient steps updates for the number of steps taken for current day every 15-30 minutes. In this example, the dots for each post-operative day lock into place at 6 am each day. For example, the dot at day 0 is number of steps taken from time of surgery until 6 am the following day, then day 1 begins at 6 am on the first morning after surgery. The interface 300 in FIG. 3A therefore shows a step count by postoperative day compared to an average patient, across all postoperative days. This representation of longitudinal step count over a number of days is specific to each surgery type, since standardized trajectory of step count for ambulation differs by surgery type. The average patient data for each surgery is gathered from patients undergoing the surgery type and compiled by applications run on the health care institution server 130 in FIG. 1

The interface 350 in FIG. 3B shows the number of steps taken for the current day versus the step goal in an ambulation routine. In this example, the daily goal is 1000 steps. This view in the interface 350 is generic to all surgery types. The interface 350 allows a real-time assessment of number of steps toward a daily goal of 1000 steps for ambulation. Of course different numbers of steps may be provided for goals and may be set by the health care professional on the application to generate the interface 350. In this example, a full circle represents 1000 steps. A red circular bar 352 and a yellow icon such as a walking man 354 represent the progress of the patient toward completing the step goal. A completion icon such as a green walking man icon 356 represents the goal pace. In this example, the completion icon 356 moves around the circular bar 352 at a rate of 0.694 steps/minute (1000 steps/24 hours) in this example. The patient's progress in ambulation will ideally be updated every 15-30 minutes in this example based on ambulation step data obtained from the biosensor device 104 in FIG. 1. The update will be reflected in the movement of the walking man icon 354 relative to the red circular bar 352 in the interface 350 in FIG. 3B.

The interface 350 also includes a data field 360. In this example, the data field 360 includes a "steps today" field 362 that displays the number of steps taken by the patient since 6 am. A "goal pace" field 364 represents the number of goal steps, which is the number of steps taken by green walking man icon 356. In this example, all of the step numbers are reset at 6 am daily.

Another mechanism to provide an indication to the patient on their progress could be a display on the biosensor device 104 in FIG. 1. For example, the biosensor device 104 may include a color indicator that corresponds with the number of steps taken toward the ambulation goal. For example, the colors may range from red to green and different colors may be displayed to the patient as additional steps are taken.

The example system also incentivizes patients to complete daily ambulatory therapy by offering predetermined tours of lengths consistent with the steps for ambulation goals. For example, such tours may be specific routes through a health care institution. One specific example may be determining routes where patients may ambulate throughout different parts of a health care institution. A patient may be supplied with instructions or instructions may be downloaded into an application for display on a mobile device such as the device 120 in FIG. 1.

An example of such a tour could be an "art tour" where a patient is given a route of a predetermined number of steps to view hospital art work. Given the significant relationship between biosensor-measured step count and efficiency outcomes, it is important for the surgical team to be able to engage patients in meeting step count goals and to prescribe specific walking courses that correspond to certain number of steps. By establishing different courses relating to an "art tour" on the medical/surgical floors that correspond to discrete step counts, the surgical team can prescribe specific courses to allow the patient to achieve daily step count goals. However, the medium for incentivizing patients to complete the ambulation goals may differ from hospital to hospital.

To further engage patients in achieving their step count goals, "art tours" and an "art tour" application may be created for the mobile user device 120 in FIG. 1. Such an application provides verbal and written narration on the museum-quality art pieces displayed on the medical/surgical floors at an example health care building. The application would include the narration corresponding to the art pieces a patient would encounter on each walking course mentioned above. The application allows patients to call up each art piece by its inventory number, shows a picture of the art piece, and provides written and verbal narration to accompany each piece.

Figures 4A, 4B:
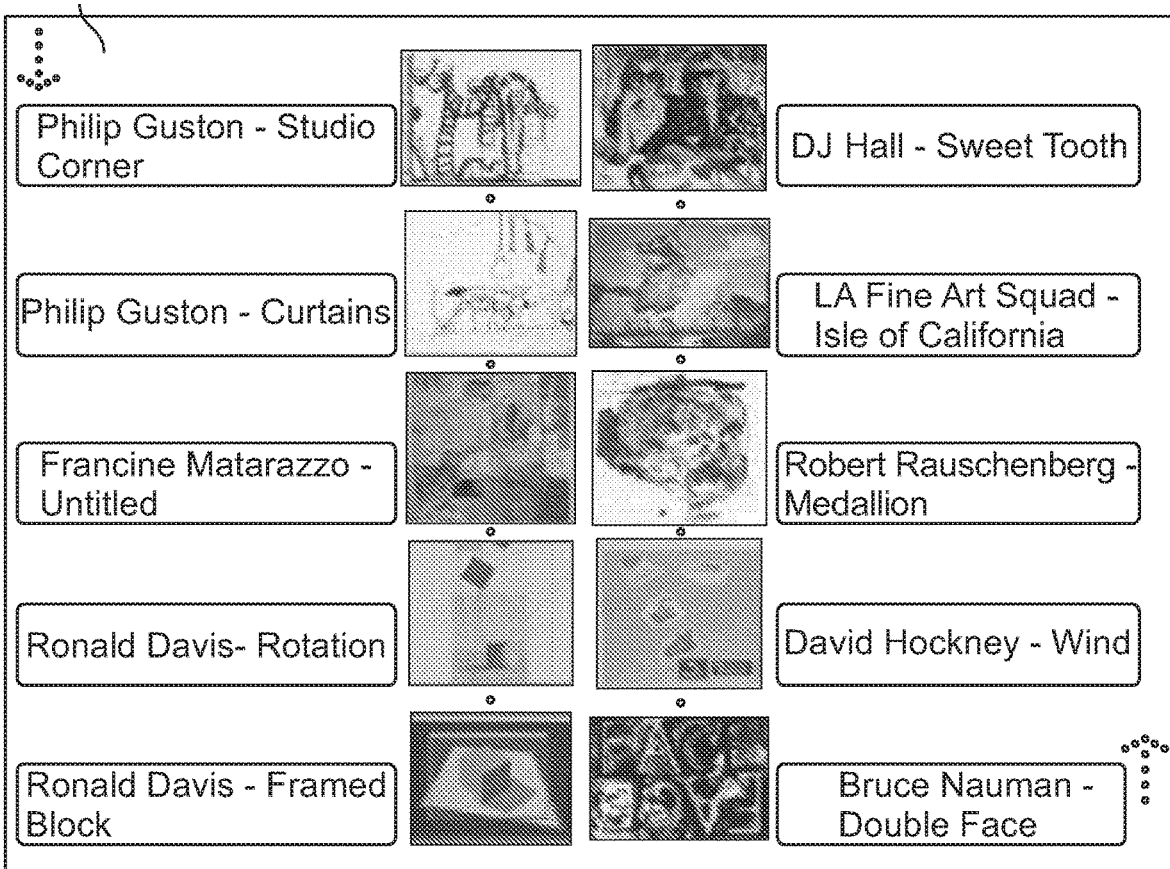
FIGS. 4A-4B are guide descriptions for an art tour used for patient ambulation routines.

FIG. 4A shows a course description 400 that gives a patient instructions to ambulate to different goals such as art work that is at different physical locations in a medical institution such as a hospital. Each of the goals in a route is art work at different physical locations. The number of steps between each art goal allows a route to be tailored to a specific ambulation objective. FIG. 4B shows a visual description 450 showing the art work at each of the locations to assist the patient in determining if a particular goal is achieved. Different courses of different goals may be provided to a patient based on the ambulation goals for a particular day and a particular surgery type. The descriptions 400 and 450 may be provided to the patient in a physical form such as a booklet, or may be displayed on a mobile device.

Figure 4C:
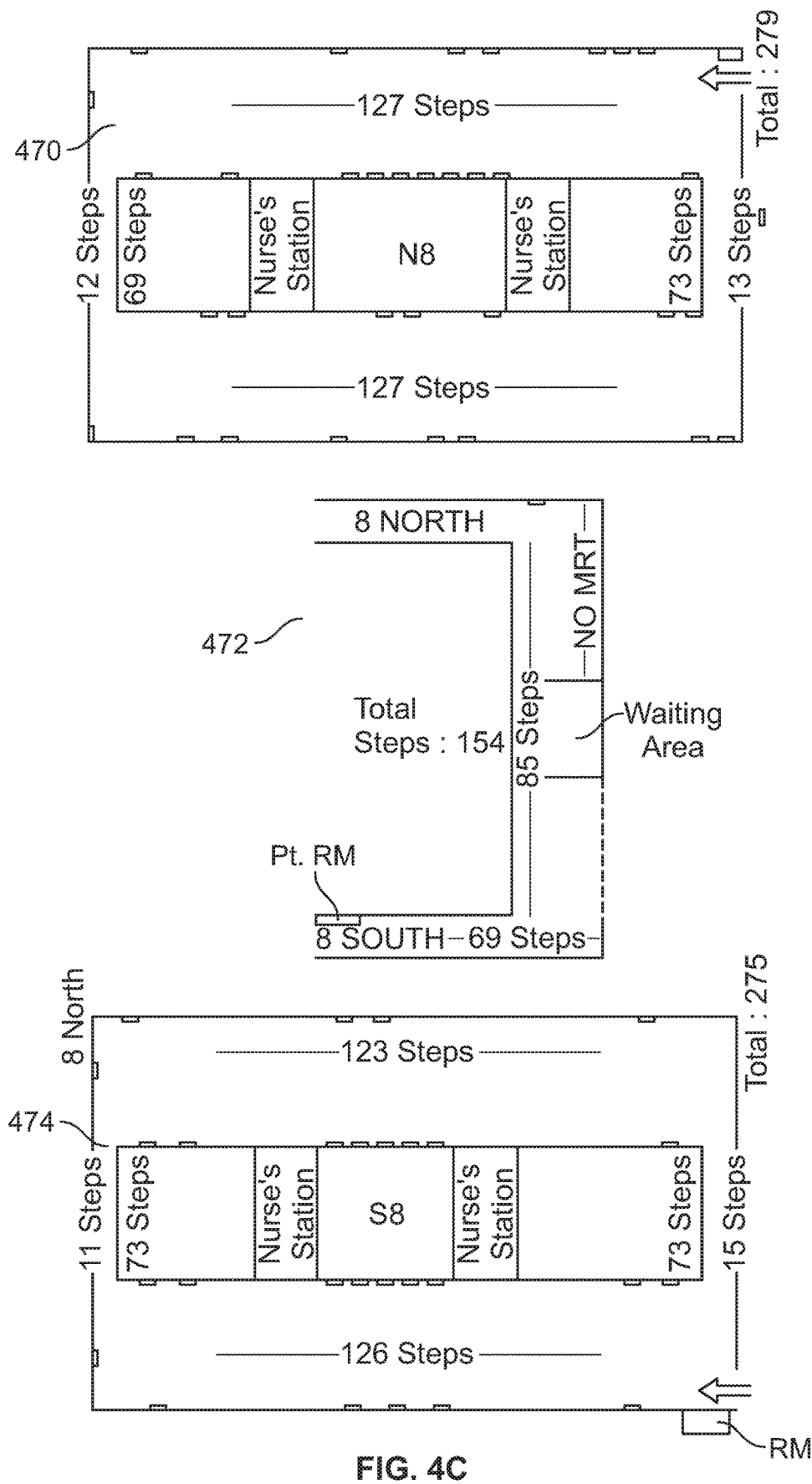
FIG. 4C are step count maps for the art tour in FIGS. 4A-4B.

FIG. 4C shows maps 470, 472 and 474 of an example health care building that correspond to specific desirable step counts. The example map 470 reflects a first course (course A) that is a full lap around the north or south wing of each unit, which corresponds to 279 steps. The example map 472 reflects another course (Course B) is the east-west hallway on the north or south side of each unit, which is 127 steps in each direction (254 steps round trip). The example map 474 reflects another course (Course C) involves walking the length of the east-west hallway (125 steps each way), then continuing across the "bridge connecting the north and south wings (154 steps each way), with a round trip corresponding to 558 steps in total (roughly 550 steps). The example step counts in the maps 470, 472 and 474 are specific to floor plans at an example health care building but could be applied to any hospital environment using a similar method.

The art tours correspond to the courses mentioned above, and are detailed in FIGS. 4A-4B. The two "Inner Tours" for each floor correspond to Course A above (279 steps). The two "Outer Tours" for each floor correspond to Course B above (254 steps). The concept of art tours leverages a unique art collection but could be adapted for any interactive experience at other hospitals; for example, images of local history, moments in sports, biographies, or other media could be used to engage patients rather than art pieces.

The success of tracking ambulation in increasing post operative patients is shown by a study involving participants that were patients undergoing eight major inpatient surgeries (robotic cystectomy, open colectomy, laparoscopic/robotic colectomy, abdominal hysterectomy, lung lobectomy, gastric bypass, hip replacement, and sleeve gastrectomy) at Cedars-Sinai Medical Center. In order to be eligible for the study, a patient was: 18 years of age or older; undergoing robotic cystectomy, open colectomy, abdominal hysterectomy, esophagectomy, lung lobectomy, gastric bypass, hip replacement, laparoscopic/robotic colectomy, and sleeve gastrectomy; non-English speakers; and able to provide informed consent. Patients were excluded from the study if they were: unable to provide consent; not undergoing the procedure of interest; admitted to the ICU after the operation (with exception of esophagectomy patients, who are all admitted to the ICU after the operation); use of a walker, cane, or wheelchair at baseline; unable to walk due to physical limitation; residing in a skilled nursing facility at baseline; unable to maintain the biosensor in place due to cognitive impairment; or were unable to wear the biosensor on their wrist.

The study aimed to enroll 20 patients per procedure, with an accrual goal of 180 total subjects. The study team screened upcoming case schedules of co-investigators to help identify potential participants. Urologists, colorectal surgeons, orthopedic surgeons, and gynecologists referred patients for the study. Recruitment was conducted in the outpatient setting at the time of treatment counseling. Among 135 subjects consented, 8 were dropped due to cancellation of surgery, 3 due to refusal to participate postoperatively, and 16 due to loss of the Fitbit device or data.

After the subject was awake and alert after surgery, a study team member placed the Fitbit Charge® wearable biosensor on their wrist. Subjects were encouraged to keep the device in place throughout their hospitalization, except while showering. Daily step count was passively monitored for the duration of hospitalization, with the option to discontinue if clinically required or requested by the patient or provider. Wearable biosensor devices were recharged as needed (generally every 5-7 days). Data from the wearable biosensor was uploaded via a secure Bluetooth connection at the time of discharge. Data from the Fitbit devices was uploaded into the research team's computer via a secure Bluetooth connection. Fitbit accounts were created for each participant using a unique study identification (SID) number instead of patient personal information, and all participant activity data will be associated with this SID number. No personal information was be collected or transmitted by the Fitbit devices or appear on participants' Fitbit accounts. The document linking participants' personal information to their SID was stored in a password-protected computer within a firewall, or in a locked cabinet in the study location.

The daily step count was measured as number of steps taken from 6 am-6 pm on the indicated postoperative day. The postoperative day 0 was defined as the day of surgery. An ordered ambulation regimen for each postoperative day as entered by the provider team as part of routine practice was retrospectively ascertained from the medical record. Surgeons were asked to record their estimate of the subject's ambulation the day prior in progress notes documenting morning rounds. Surgeons were asked to use standardized terms to categorize the degree of ambulation based on terminology commonly used in the surgical vernacular: nonambulatory; out of bed to chair; out of bed to ambulate daily, twice daily, or three times daily; or ambulating ad lib. Additional sociodemographic (age, gender, race/ethnicity) and clinical data (body mass index, comorbid health conditions) was collected by review of the medical record for the subject patients.

Physicians participating in the study provided data on estimated daily ambulation, using a standard formatted scale. Surgeons currently assess daily ambulation in the medical record, but assessments are not uniform, which precludes meaningful comparisons between providers. The physicians recorded daily estimates of ambulatory status according to standardized terms that are commonly used in the medical record (nonambulatory; out of bed to chair; out of bed to ambulate (QD, BID, TID); and ambulating ad lib). Information on daily ambulation orders as entered by the provider team as part of routine practice was collected. This information was ascertained by chart review and entered into the secure spreadsheet along with the additional patient data.

Several methods were used to determine date of discharge from the hospital. At the time of discharge, a study team member removed the biosensor device from the patient and downloaded the information from the device to an IRB-approved spreadsheet. The wearable biosensor was reset at that time and the information was erased from its memory.

The medical records were queried for information regarding disposition outcomes, including length of stay (from end of surgery to discharge from the hospital) and location of disposition (to home, rehab facility, or skilled nursing facility). Follow up contact of the patients by phone was made after 30 days have elapsed since discharge to inquire whether they have been readmitted to the hospital or ER within the 30 days of their discharge date.

To illustrate the average trajectory and distribution of postoperative ambulation, boxplots depicting biosensor-measured steps taken by postoperative day were created. Separate boxplots were used to show data in aggregate across all surgeries and for each procedure.

To visually describe how biosensor-measured daily step count correlates with surgeons' estimation of patient ambulation, biosensor-measured step counts were plotted across different categories of daily ambulation estimates (out of bed to chair; out of bed to ambulate daily, twice daily, or three times daily; or ambulating ad lib). A similar method was used to describe how biosensor-measured daily step count correlates with ordered daily ambulation regimen, we plotted biosensor-measured step count across different ambulation orders in the electronic medical record. Given uniformity of data, data in aggregate across all surgeries was only considered.

To determine if biosensor-measured daily step count predicts surgery-specific length of stay, linear regression analysis with cubic splines was used. The study used $p<0.05$ to denote statistical significance of two-sided tests. All statistical analyses were performed in Stata 11.0 (Stata Inc., College Station, Tex.).

Wearable biosensors such the Fitbit device provided a simple, inexpensive, and scalable method for quantifying postoperative ambulation. While standard pedometer technology has existed for decades, a major hurdle that prevented scaling of this technology was the inability to easily integrate this information into the medical record. Cedars-Sinai Enterprise Information Services (EIS) has achieved the largest integration to date between an electronic health record (EHR), mHealth applications, and wearable biosensors. Patients have direct and secure connectivity between their digital devices and the Epic HER. PRI data may be remoted monitored as part of everyday care.

The ability to collect large amounts of data remotely through the EHR could provide the opportunity to create a real-time, constantly updating standard for monitoring postoperative ambulation across numerous procedures and across specialties. Furthermore, Cedars-Sinai has one of the highest surgical volumes in the United States, performing 16,753 inpatient surgeries annually. This provides an unprecedented, large-scale opportunity to standardize paradigms for using this technology in the daily care of surgical patients.

Monitoring of postoperative ambulation is most critical in the setting of surgeries that may impact ambulatory status and that have substantial length of stay. Nine major surgeries are commonly performed at Cedars-Sinai that currently have a reported average length of stay longer than 3 days and affect ambulatory status: robotic cystectomy, open colectomy, abdominal hysterectomy, esophagectomy, lung lobectomy, gastric bypass, hip replacement, laparoscopic/robotic colectomy, and sleeve gastrectomy. The standard trajectories for postoperative ambulation differ by type of surgery; for example, the number of steps taken on post-operative day 1 after a radical cystectomy will differ from the same measurement taken after a hip replacement. By creating standardized trajectories for ambulation that are specific to a given procedure, deviation from the expected may be accurately obtained.

Quantitative measurement of postoperative ambulation may be used to predict key recovery and disposition outcomes. This measurement provides an opportunity for meaningful intervention. This data may be used as a "sixth vital sign" for surgical inpatients. Integration of this information with the EHR (which is entirely feasible based on existing infrastructure) would provide a system that monitors patients continuously, providing meaningful and actionable data to providers in real-time, and driving decision-making that is timely and proactive, not late and reactive.

Figure 5:
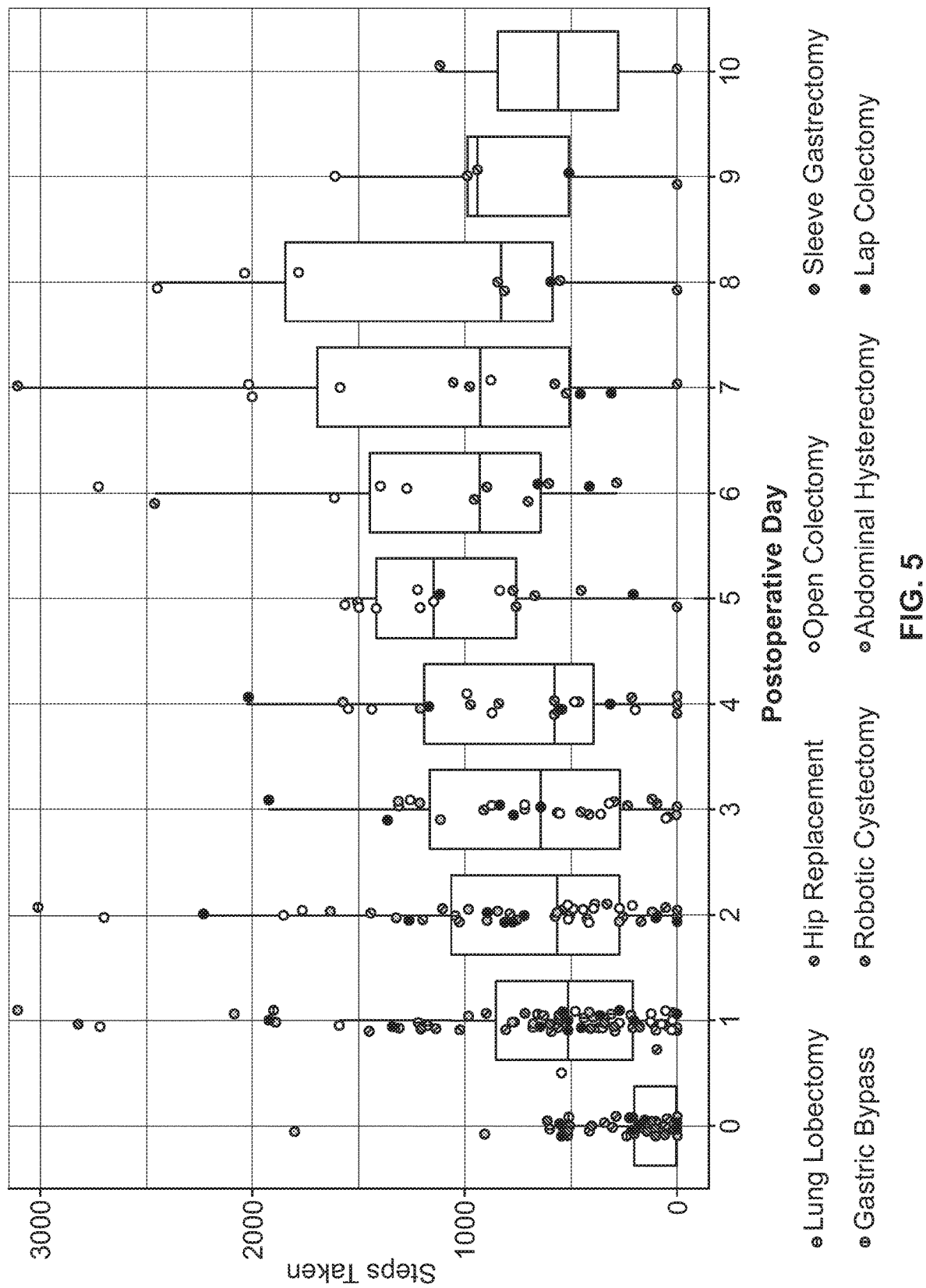
FIG. 5 is a series of boxplots depicting biosensor-measured daily step count by postoperative day across all surgeries.

FIG. 5 shows boxplots depicting biosensor-measured daily step count by postoperative day across all surgeries that show a gradual increase in step count with each successive postoperative day until a plateau at approximately postoperative day 5. Median daily step count (IQR) increased from 0 (0, 211) on day 0, 497 (815, 830) on day 1, 565 (956, 1078) on day 2, 566 (921, 1118) on day 3, 676 (902, 1182) on day 4, to 1136 (1257, 1418) on day 5. The Pearson correlation coefficient showed a statistically significant increasing trend between daily step count and postoperative day (r=0.26, 95% CI: 0.16-0.35 p<0.001). There was also substantial variability in range of steps taken, especially among early postoperative days. For example, biosensor-measured steps on postoperative day 1 ranged from 0-7698. The result from Bartlett's test for homogeneity of variances showed significant differences in variances of steps taken among all post-operative days (p<0.001).

Figure 6:
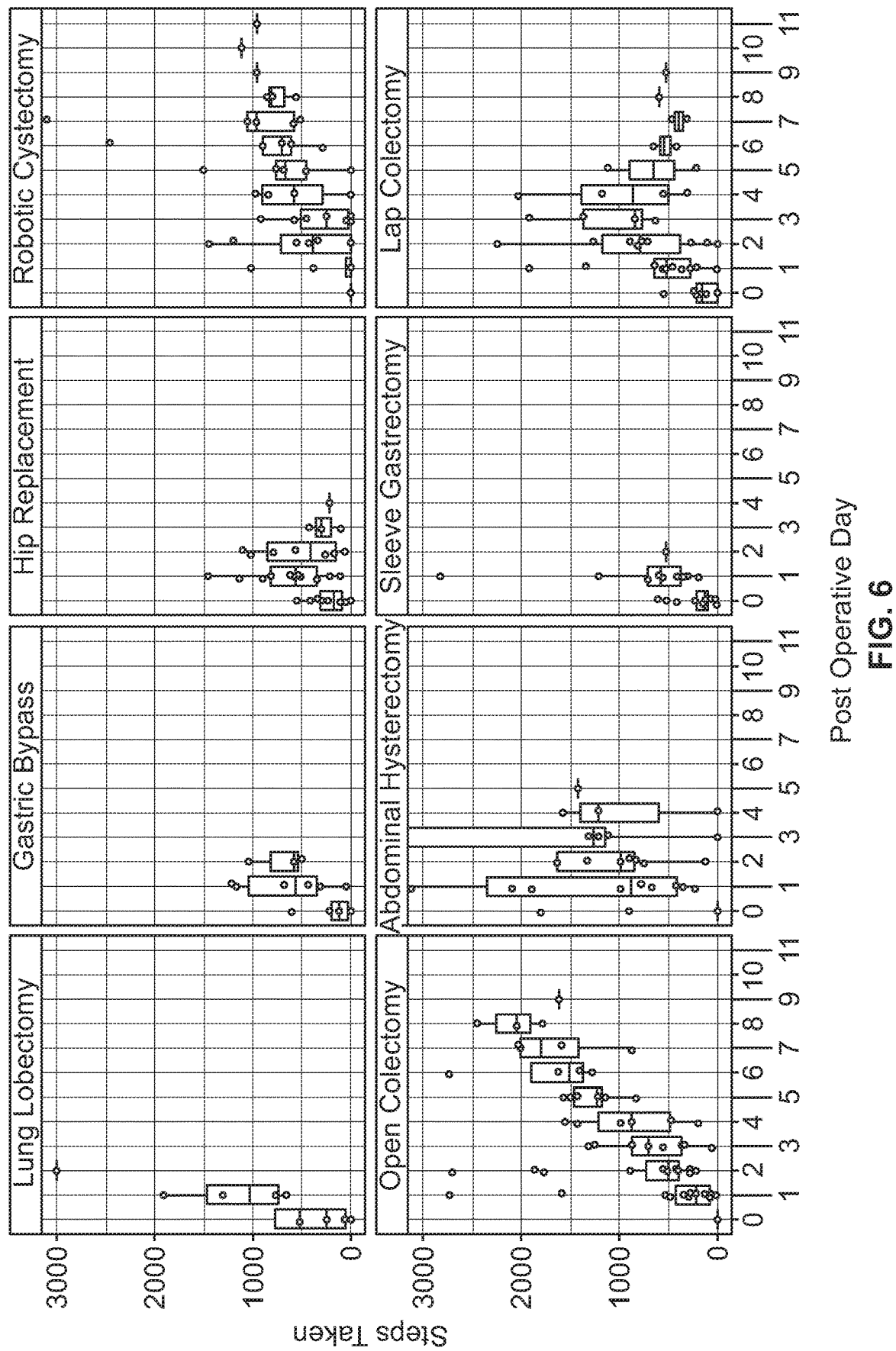
FIG. 6 is a series of boxplots depicting biosensor-measured daily step count by postoperative day across individual surgery type.

FIG. 6 shows boxplots depicting biosensor-measured daily step count by postoperative day across individual surgery type revealed differences in step count according to surgery type. In general, median step count increased with successive postoperative days, similar to the trend seen in the aggregate analysis.

Figure 7:
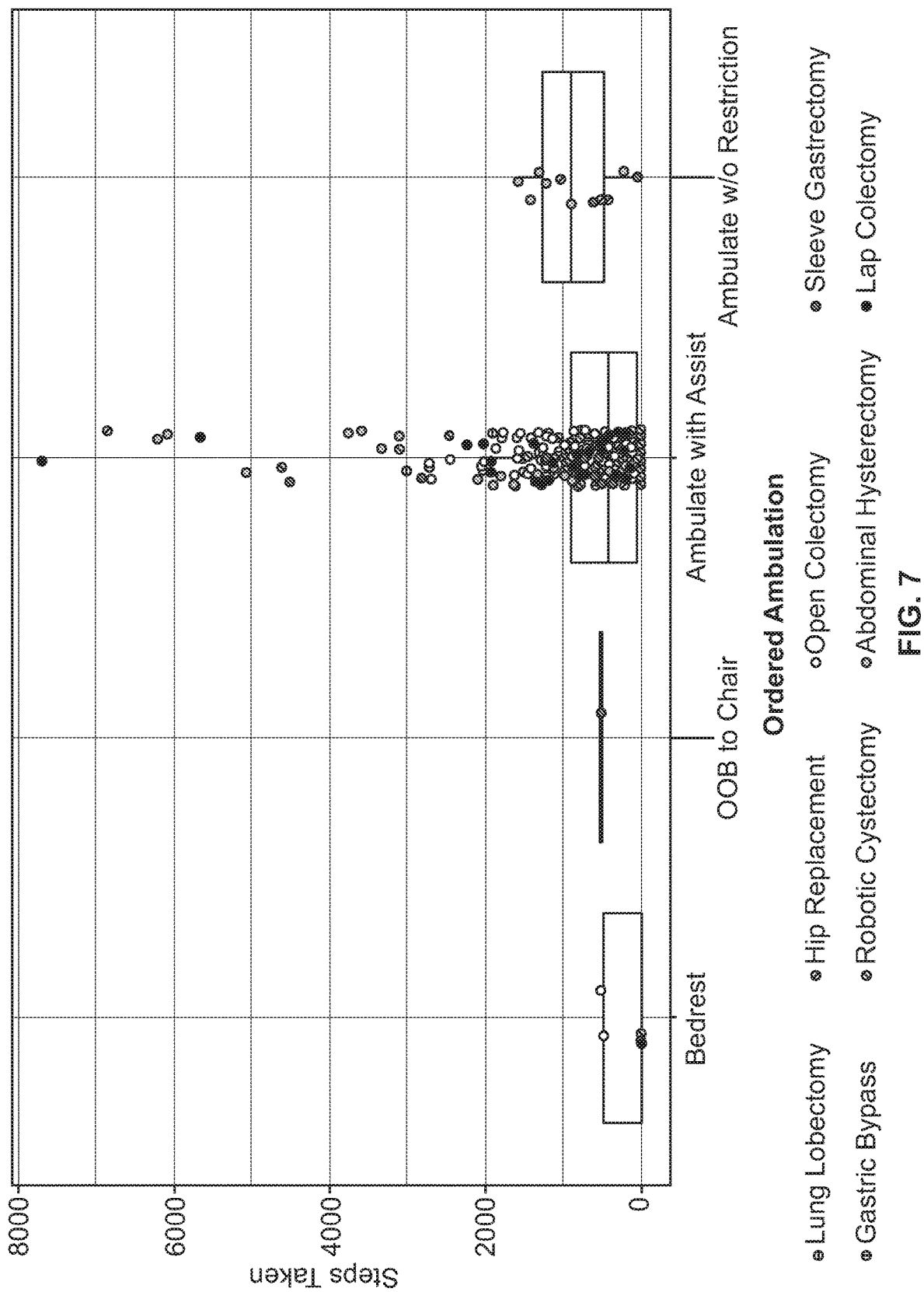
FIG. 7 is a series of boxplots showing biosensor-measured daily step count by ordered daily ambulation regimen.

FIG. 7 shows boxplots showing biosensor-measured daily step count by ordered daily ambulation regimen showed uniformity in ordered ambulation regimen despite a wide range of steps taken. For example, 95% of orders were for "ambulation with assistance," which included a range of step counts from 0-7698.

Figure 8:
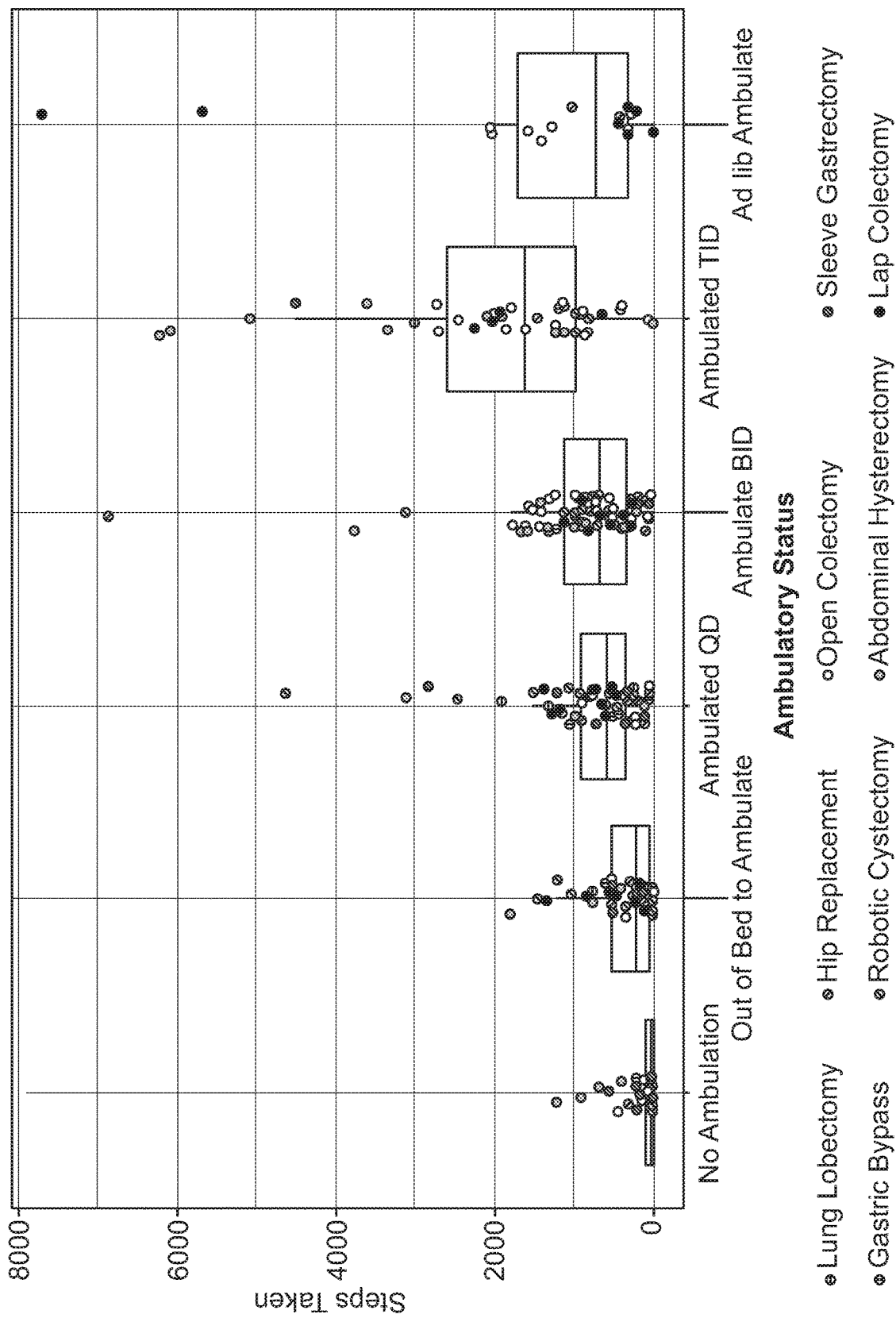
FIG. 8 is a series of box plots of biosensor measured step count versus surgeon estimate of step count.

FIG. 8 shows boxplots of biosensor measured step count versus surgeon estimate of step count. Surgeon estimates of daily ambulation accurately reflected a trend toward increasing median biosensor-measured step count with categories indicating greater ambulation as shown in FIG. 8. However, there was substantial range of step count within these categories. For example, patients who were thought to be "out of bed to ambulate" around their hospital room had step counts ranging from 0-1803 steps.

Figure 9:
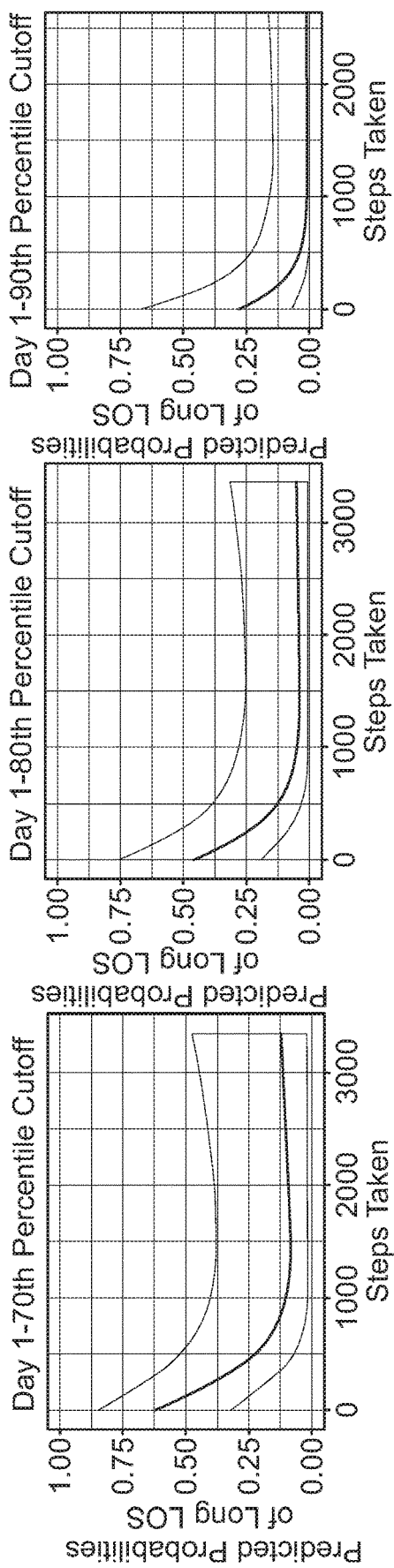
FIG. 9 is a series of graphs showing predicted probabilities of surgery-specific length of stay longer than different percentiles.
Figure 9:
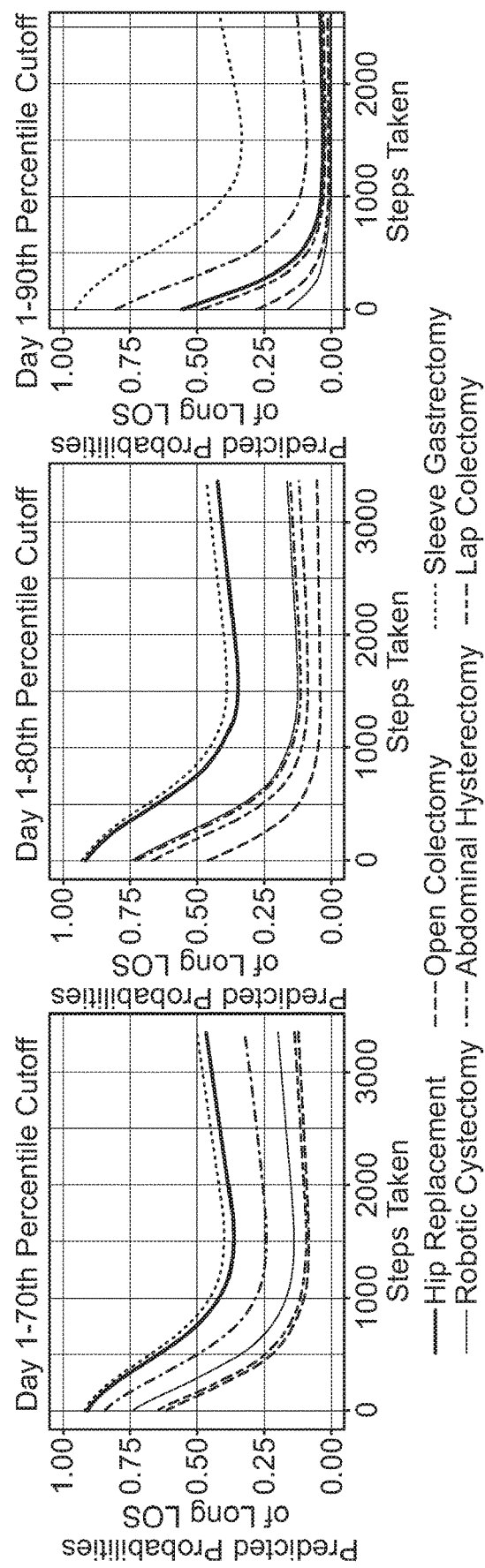

FIG. 9 shows predicted probabilities of surgery-specific length of stay longer than different percentiles. These percentiles included $70^{th}$ percentile, $80^{th}$ percentile, and $90^{th}$ percentile by postoperative day 1 step count across all Surgeries in graphs A-C and by type of surgery in graphs D-F.

Multivariable linear regression models with cubic splines predicting surgery-specific length of stay showed that step count on postoperative day 1 was significantly associated with length of stay.

Wearable biosensor-measured step count at early timepoints in the post-operative course is a strong predictor of surgery-specific length of stay. While the association between step count and length of stay is already known, this study provides critical benchmark data linking wearable biosensor data with a clinically meaningful endpoint. A higher number of biosensor-measured steps on day one was linearly associated with overall length of stay until a step count of 1000, beyond which there was little added benefit of further ambulation. For each successive increase in 100 steps toward the goal of 1000, there was an approximately 5% reduction in the probability of the length of stay being in the upper 70th percentile for a given surgery. For a patient who takes no steps in the first postoperative day, there was a 75% probability of LOS >70th percentile, in comparison to 25% probability for a patient who took 1000 steps. This association held up across surgeries and the outcome was surgery specific. This work provides the critical foundation for building an interventional approach using wearables going forward. This study overcomes the hurdle that potentially has hampered the success of other prospective studies of wearables have been negative: there is a target for interventional work.

Despite its clear importance to efficiency and clinical outcomes, data shows that ambulation is currently only crudely measured by physicians. Doctors were able to identify increasing ambulation in their patients on average, but there was striking variability in the number of steps taken for a given estimate. For example, in patients who were estimated by physicians to have taken no steps, the range of biosensor-measured step count ranged from 0-2000 (roughly 0-0.8 miles). That physicians are not more accurately measuring such a critical determinant of key outcomes seems outdated in the era of precision medicine, though this assertion is contingent on the finding that such granularity of assessment is clinically meaningful. Since the number of steps from 0 to 1000 is significantly associated with length of stay, the degree of variability in imprecision among patients estimated to have no ambulation could certainly be clinically relevant. This supports integration of wearable biosensors to improve the granularity of assessment of postoperative step count.

There was no variability in ordering daily ambulation by provider teams, which is emblematic of the lack of precision with which ambulation is currently managed. The data shows that 97% of orders were "ambulate with assistance," despite other available orders for "bedrest", "OOB to chair", and "ambulate ad lib." Among those ordered to "ambulate with assistance," actual step count ranged between 0-8000 steps. The lack of granularity in ordering may be partially contributing to the wide variety of steps taken usnder this order, and potentially to the variability in daily step count among patients globally.

Wearable biosensors for measuring postop ambulation is a method that is scalable and can be integrated seamlessly into current electronic medical records (EMR)s. Although pedometers have existed for a long time, the feasibility of integrating serial measurement, feedback with these devices into busy workflows would be prohibitively cumbersome. Yet wearable biosensors make easy integration of this data and possible feedback to relevant stakeholder not only feasible but relatively straightforward.

Thus, the system is based on the concept of using a wearable biosensor device to monitor postoperative ambulation after major surgery to identify patients at risk for poor outcomes (e.g. long length of stay) (diagnostic tool). The system also includes predictive algorithms to operationalize step count data from wearable biosensors to predict length of stay (algorithm). Case management may also be enhanced. For example, if deviations from the standard ambulation trajectory as early as post-operative day 1 or 2 significantly predict disposition to rehab/skilled nursing, then case management may be alerted at that time to prevent delays in placement that could increase costs of the inpatient hospital stay.

FIG. 10 is a table showing the probability of length of stay of patients by step count in the aggregate. The breakdown of length of stay of patients by surgical procedure type is attached in a table in FIGS. 11A-11B.

The terminology used herein is for the purpose of describing particular embodiments only, and is not intended to be limiting of the invention. As used herein, the singular forms "a," "an" and "the" are intended to include the plural forms as well, unless the context clearly indicates otherwise. Furthermore, to the extent that the terms "including", "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore terms, such as those defined in commonly used dictionaries, should be interpreted as having a meaning that is consistent with their meaning in the context of the relevant art, and will not be interpreted in an idealized or overly formal sense unless expressly so defined herein.

While various embodiments of the present invention have been described above, it should be understood that they have been presented by way of example only, and not limitation. Numerous changes to the disclosed embodiments can be made in accordance with the disclosure herein, without departing from the spirit or scope of the invention. Thus, the breadth and scope of the present invention should not be limited by any of the above described embodiments. Rather, the scope of the invention should be defined in accordance with the following claims and their equivalents.

What is claimed is:

1. A method of monitoring ambulation therapy after a medical procedure, the method comprising:
    providing a patient with an ambulatory routine to allow the patient to achieve daily step count goals, wherein the ambulatory routine is configured on a mobile device;
    displaying a guide description on a display of the mobile device for a tour used for the ambulatory routine, the displayed guide description including:
    a course description providing the patient with instructions to ambulate to a particular goal, the course description including a route tailored to the particular goal such that a different number of pieces for an interactive experience are included in the route for a different goal,
    wherein different pieces are at different physical locations of a specific place;
    and information or images of the different pieces located at the different physical locations to assist the patient in determining if the particular goal is achieved,
    wherein a specific number of steps is set between two different pieces such that a total number of steps corresponding to the particular goal is determined by a set of different pieces included in the route tailored to the particular goal;
    providing, via the display of the mobile device, different courses of different goals to the patient based on an ambulation goal for a particular day and a type of the medical procedure the patient underwent,
    wherein different sets of images and/or different numbers of images are included in the different courses;
    monitoring the ambulatory routine using a wearable biosensor device configured to track steps of the patient;
    recording the steps of the patient in following the ambulatory routine;
    transmitting ambulation data, collected by the biosensor device and including the recorded steps of the patient, to a medical institution server connected to a network that allows health care professionals to monitor a status of the ambulation therapy for the patient;
    and displaying the ambulation data on an external display, which is available to the patient and the health care professionals and external to the biosensor device, on a periodic basis to provide feedback to the patient and the health care professionals, the ambulation data including data related to the recorded steps of the patient.

2. The method of claim 1, wherein the ambulation data for the patient is displayed in comparison to an average patient undergoing the medical procedure.

3. The method of claim 1, wherein the ambulation data is displayed in comparison to an ambulation goal of the ambulatory routine.

4. The method of claim 1, further comprising analyzing the ambulation data to determine compliance with post procedure metrics.

5. The method of claim 1, further comprising displaying a map of the route corresponding to the tour according to the ambulatory routine corresponding to the particular goal on the display of the mobile device to guide the patient.

6. The method of claim 1, wherein the recorded steps are stored in the medical institution server accessible by the health care professionals.

7. The method of claim 1, further comprising displaying progress of ambulation on the display of the mobile device in real time.

8. The method of claim 1, wherein the ambulation data is further displayed on a display device accessible to the patient and/or health care professionals, a display of the biosensor device, the display of the mobile device, or combinations thereof.

9. The method of claim 1, wherein:
    the specific place includes a health care/medical institution, a hospital, or a building,
    the different physical locations include different floor plans of the health care/medical institution, the hospital, or the building,
    and the external display includes an in-room TV screen at the specific place.

10. The method of claim 1, wherein:
the pieces for an interactive experience include art pieces displayed at the different physical locations;
the method further comprises displaying, on the display of the mobile device, descriptions of the art pieces;
and the descriptions include at least artist names, titles of the art pieces, or years the art pieces were completed.

11. The method of claim 1, further comprising providing the patient with a different ambulatory routine to allow the patient to achieve a step count goal tailored to an ambulation goal set for another day.

12. The method of claim 1, wherein each course of the different courses includes a different set of images corresponding to a different number of steps.

13. A method of analyzing ambulation data from a plurality of patients after a medical procedure, the method comprising:
assigning each patient of the plurality of patients a wearable biosensor device after the plurality of patients undergo the medical procedure;
displaying on a display of a mobile device assigned to each patient of the plurality of patients a daily ambulatory routine to allow each patient to achieve daily step count goals;
displaying a guide description on the display of the mobile device assigned to each patient for a tour used for the daily ambulatory routine, the displayed guide description including:
a course description providing each patient with instructions to ambulate to a particular goal, the course description including a route tailored to the particular goal such that a different number of pieces for an interactive experience are included in the route for a different goal,
wherein different pieces are at different physical locations of a specific place;
and information or images of the different pieces located at the different physical locations to assist each patient in determining if the particular goal is achieved,
wherein a specific number of steps is set between two different pieces such that a total number of steps corresponding to the particular goal is determined by a set of different pieces included in the route tailored to the particular goal;
providing, via the display of the mobile device assigned to each patient, different courses of different goals to each patient based on an ambulation goal for a particular day and a type of the medical procedure each patient underwent,
wherein different sets of images and/or different numbers of images are included in the different courses;
recording step data from the biosensor device associated with each patient of the plurality of patients;
transmitting ambulation data for each patient, collected by the biosensor device associated with each patient and including the recorded step data of each patient, to a medical institution server connected to a network that allows health care professionals to monitor a status of the ambulation data for each patient;
and analyzing the ambulation data for each patient including the recorded step data to determine optimal steps for the ambulatory routine associated with the medical procedure.

14. The method of claim 13, wherein the ambulation data for each patient is displayed in comparison to an average patient undergoing the medical procedure.

15. The method of claim 13, wherein the ambulation data for each patient is displayed in comparison to an ambulation goal of the ambulatory routine.

16. The method of claim 13, further comprising analyzing the ambulation data for each patient at to determine compliance with post procedure metrics.

17. The method of claim 13, further comprising displaying a map of the route corresponding to the tour according to the ambulatory routine corresponding to the particular goal of each patient on the display of the mobile device associated with each patient to guide each patient.

18. The method of claim 13, wherein the recorded step data are stored in the medical institution server accessible by the health care professionals.

19. The method of claim 13, further comprising displaying progress of ambulation on the display of the mobile device in real time.

20. The method of claim 13, further comprising displaying the ambulation data for each patient on an external display available to each patient and the health care professionals and external to the biosensor device,
the external display including an in-room TV screen at the specific place including a health care/medical institution, a hospital, or a building.

21. The method of claim 13, further comprising displaying the ambulation data for each patient on a display device accessible to each of the patients and/or the health care professionals, a display of the biosensor device, the display of the mobile device, or combinations thereof.

* * * * *